United States Patent [19]

Drost et al.

[11] Patent Number: 5,395,556
[45] Date of Patent: Mar. 7, 1995

[54] TRICYANOVINYL SUBSTITUTION PROCESS FOR NLO POLYMERS

[75] Inventors: Kevin J. Drost, North Brunswick; Pushkara R. Varanasi, Monmouth Junction; Kwan-Yue A. Jen, Old Bridge; Michael A. Drzewinski, Princeton Junction, all of N.J.

[73] Assignee: Enichem S.p.A., Italy

[21] Appl. No.: 773,708

[22] Filed: Oct. 9, 1991

Related U.S. Application Data

[63] Continuation-in-part of Ser. No. 626,358, Dec. 12, 1990, abandoned.

[51] Int. Cl.$^6$ .............. F21V 9/00; C08G 59/00; C08G 73/06
[52] U.S. Cl. .................... 252/582; 252/587; 526/256; 526/257; 526/258; 526/259; 526/261; 526/266; 526/267; 526/270; 528/403; 528/405; 528/407; 528/423
[58] Field of Search ............ 252/582, 587, 589; 526/257, 256, 258, 259, 261, 266, 267, 270; 528/403, 405, 407, 423

[56] References Cited

U.S. PATENT DOCUMENTS

| | | | |
|---|---|---|---|
| 3,978,029 | 8/1976 | Limburg | 526/260 |
| 4,892,681 | 1/1990 | Miyata et al. | 252/582 |
| 4,894,186 | 1/1990 | Gordon et al. | 252/582 |
| 4,894,263 | 1/1990 | Dubois et al. | 428/1 |
| 4,933,112 | 6/1990 | DeMartino et al. | 252/587 |
| 4,935,292 | 6/1990 | Marks et al. | 428/220 |
| 4,946,629 | 8/1990 | Allen et al. | 252/582 |
| 4,985,325 | 1/1991 | Kuroda et al. | 252/582 |
| 5,061,404 | 11/1991 | Wu et al. | 252/502 |

FOREIGN PATENT DOCUMENTS

| | | |
|---|---|---|
| 2010528 | 8/1990 | Canada. |
| WO90/09616 | 8/1990 | WIPO. |

OTHER PUBLICATIONS

Oshiro et al., *Polym. J.*, 6(5), 364–369 (1974).
Tazuke et al., *Makromol. Chem.*, 181, 2199–2206 (1980).

*Primary Examiner*—Philip Tucker
*Attorney, Agent, or Firm*—Lerner, David, Littenberg, Krumholz & Mentlik

[57] ABSTRACT

Base polymers devoid of non-linear optical properties exhibiting second order non-linear optical properties after the covalent attachment of tricyanovinyl groups to pendant side chains of the base polymer. Methods of preparing a polymer having second order non-linear optical properties by reacting the base polymers of the present invention with tetracyanoethylene in a basic solvent at elevated temperatures.

20 Claims, No Drawings

TRICYANOVINYL SUBSTITUTION PROCESS FOR NLO POLYMERS

This is a continuation-in-part of U.S. patent application Ser. No. 626,358, filed Dec. 12, 1990, now abandoned.

BACKGROUND OF THE INVENTION

1. Field of the Invention

The present invention relates to heteroaromatic compounds with nonlinear optical properties. In particular, the present invention relates to nonlinear optical materials having highly conjugated structures with two or more aromatic rings, at least one of which is a five-membered heteroaromatic ring. The compounds of the present invention, once suitably oriented, are capable of highly efficient second harmonic generation (SHG) and electro-optic modulation of an electromagnetic wave whose wavelength may be between 300 nm and 2000 nm. The present invention further relates to the incorporation of the compounds of the present invention into polymeric matrices, including polymers having side chains of the disclosed compounds.

2. Description of the Prior Art

High efficiency nonlinear optical (NLO) materials capable of doubling or tripling the frequency of incident light are currently of great scientific and technological interest for use in optical telecommunications, signal processing and the construction of optical computers. Nonlinear optics is concerned with the interaction of electromagnetic fields in various media to produce new fields which may be altered in phase, frequency or amplitude. The NLO effect of a material upon an electromagnetic field is a function of the second and higher order terms of the following equation:

$$P = \alpha E + \beta E^2 + \gamma E^3 +$$

P is the polarization of the material, E is the intensity of the electric field, and the coefficients alpha, beta, gamma, etc. are indicative of the NLO susceptibility of the material. Such coefficients are constant for a given material, but vary from material to material. The second order coefficient, beta, for a given material, is indicative of the SHG properties of the material, with SHG efficiencies increasing as the value of beta increases.

Candidate NLO materials should possess good physical properties, such as high optical transparency, low dielectric constant, high laser damage threshold, good solubility in the solvents used for spin casting of optical materials, and the like. The materials should also possess the mechanical and thermal properties required of optical materials, in particular, high beta values, fast response times and nonlinear susceptibility over a broad range of wavelengths, particularly at wavelengths between about 300 nm and about 2000 nm.

The first NLO materials were monocrystal minerals such as $KH_2PO_4$, $LiNbO_3$, InSb and $NH_4H_2PO_4$. However, these materials are costly to grow in high optical quality and show relatively low SHG properties. These materials are expected to be replaced by organic and polymeric materials with large delocalized pi-electron systems, which not only exhibit greater nonlinear susceptibilities, but also can be varied to optimize the desired physical and mechanical properties.

Early organic NLO materials were based upon conjugated pi-electron chromophores with charge asymmetry, such as 4-dimethylamino-4-nitrostilbene (DANS), dissolved in a suitable polymer matrix, which are disclosed by Williams, *Angew. Chem. Int. Ed. Engl.*, 23, 690–703 (1984). However, such combinations were of limited solubility, resulting in crystallization of the guest chromophore molecule out of the host matrix, or mobility of the guest molecules in the matrix, resulting in a loss of SHG performance. Such materials are also exemplified by U.S. Pat. No. 4,892,681 to Miyata and U.S. Pat. No. 4,894,186 to Gordon.

The insolubility of these materials in a polymer matrix was overcome by the covalent linking of the NLO chromophores to the polymer backbones. This is also disclosed by Williams, as well as U.S. Pat. Nos. 4,894,263 to Dubois, 4,933,112 to DeMartino and 4,935,292 to Marks. These references disclose polymers having NLO chromophore side chains of a series of aromatic rings separated by pi-electron conjugated carbon-carbon, carbon-nitrogen and nitrogen-nitrogen bridges. The side chains utilize from two to four or greater aromatic ring/conjugated bridge combinations. The aromatic rings disclosed are based on six-membered rings such as benzene and pyridine. The chromophore side chain is covalently attached to the polymer by a reactive binding, typically a long chain alkyl group linking one of the aromatic rings of the chromophore to a reactive functional side chain of the polymer. To induce charge asymmetry, and consequently second order nonlinear polarizability, the aromatic ring attached to the reactive binding is ring-substituted with an electron donating group while the aromatic ring at the end of the chromophore is ring-substituted with an electron accepting group, and the dipoles of the chromophores are aligned, in accordance with the method described by Williams and by U.S. Pat. No. 4,935,292.

Some azomethine derived chromophores, which contain five-membered heteroaromatic rings, are disclosed as having third order NLO susceptibilities by Dirk, *Proc. SPIE-Int. Soc. Opt. Eng.*, 1147, 18–25 (1989). However, the reported third order susceptibility of these materials is low, and second order properties cannot be reasonably predicted from third order susceptibilities, let alone from low-value third order susceptibility.

Methods by which polymers having chromophore side chains may be prepared vary. U.S. Pat. No. 4,933,112 discloses the attachment of the chromophore to a monomer that is then polymerized. U.S. Pat. No. 4,935,292 discloses the attachment of the chromophore to a functionalized polymer.

U.S. Pat. No. 4,894,263 discloses that either method of attachment may be used depending on the constituents of the material. It is further disclosed that the constituents of the chromophore may be assembled in one or more steps.

As noted above, the chromophores are covalently linked to polymer backbones because of their limited solubility in polymer matrices. However, the synthesis of polymers having polar side groups such as chromophores possessing a high degree of charge asymmetry can be problematic. The limited solubility is also exhibited by the chromophores and monomer-linked chromophores in polymerization solvents, and by the chromophores in reaction solvents for linking monomers and chromophores. The electron accepting groups of chromophores possess reactivity toward radicals that, together with the low monomer solubility, results in low yields of polymers having low broad molecular weights (typically less than 15,000 daltons), low $T_g$'s and low chromophore incorporation. Among the number of electron-acceptor groups employed with NLO-chromophores is the tricyanovinyl functional group, which is preferred because it induces a large degree on nonlinearity. However, it is highly susceptible to polymerization conditions. This limits the incorporation of this functional group into polymers containing NLO-chromophores.

The tricyanovinylation of poly (N-vinylindole) and poly (3-vinylcarbazole) at attachment yields of 35% to 50% have been reported. Oshiro et als., *Polym. J.*, 6(5), 364–9 (1974) disclose the tricyanovinylation of poly (N-vinylindole) and U.S. Pat. No. 3,978,029 discloses the tricyanovinylation of poly (3-vinylcarbazole). In both publications the base polymer is reacted with tetracyanoethylene in N,N-dimethylformamide (DMF) at 50°–140° C. Yields of 35% to 50% have not been achieved to date with typical NLO chromophores.

Once polymerized, the polymer is spin-cast to form a film, which is then heated to near its glass-rubber transition temperature ($T_g$) to enhance molecular motion, including rotation of the chromophore side chains. An intense electric field is then applied to the heated film for a given length of time and the film is then cooled to well below the $T_g$ in the presence of the electric field. This results in alignment of the dipoles of the side chains, providing a system in which the NLO components are locked in a preferred orientation while at the same time covalently linked within a polymer matrix. According to U.S. Pat. No. 4,935,292, NLO efficiency can be increased by repeatedly heating the material above and then cooling it below the $T_g$ several times prior to applying the electric field. It is disclosed that this reduces the number of pinholes, voids, free volume and other anomalies that can cause short circuits during poling, and also removes residual stress from the film.

Notwithstanding these advances, there remains a need for more efficient second-order nonlinear optically active materials and methods for preparing same.

SUMMARY OF THE INVENTION

Compounds have been discovered having advantageous NLO properties such as high second order susceptibilities, good solubility and ease of functionalization. These new compounds contain two or more aromatic rings, at least one of which is a five-membered heteroaromatic ring containing one heteroatom selected from O, N, S and Se and optionally including up to three additional N-heteroatoms.

In accordance with the present invention there is provided a nonlinear optical compound corresponding to the Formula I:

$$D-(Ar-(B-)_n)_m Ar-A \qquad (I)$$

wherein each Ar is an aromatic substituent independently selected from six-membered aromatic rings, five-membered heteroaromatic rings, fused ring systems containing at least one six-membered aromatic ring and fused ring systems containing at least one five-membered heteroaromatic ring; with the proviso that at least one Ar is selected from five-membered heteroaromatic rings and fused ring systems containing at least one five-membered heteroaromatic ring. The heteroaromatic rings contain one heteroatom selected from O, N, S and Se.

B is a conjugated functional group, D is a first electron donating group and A is a first electron accepting group. The value of n for each B is independently selected from zero, one, two and three, and m is from one to nine and B, D or A are attached to a member of the heteroaromatic ring alpha to a heteroatom, and when Ar is an aromatic ring, B is attached to a member of the aromatic ring para to D, A or another B.

In one embodiment of this aspect of the invention, A is a tricyanovinyl electron accepting group that is attached to a heteroaromatic ring, alpha to the heteroatom of the ring. A non-linear optical compound in accordance with this embodiment has a structure represented by Formula IA:

$$D-(Ar-(B-)_n)_m R_7-C(CN)=C(CN)_2 \qquad (IA)$$

D, Ar, B, m and n are the same as described above with respect to Formula I. $R_7$ is a five-membered heteroaromatic ring or a fused ring system containing at least one five-membered heteroaromatic ring, which heteroaromatic ring or rings have one heteroatom selected from O, N, S and Se. The tricyanovinyl group is substituted alpha to a heteroatom.

One aspect of the present invention provides non-centrosymmetric crystals of the above mentioned compounds for use as second order nonlinear optical materials.

Another aspect of the present invention provides a combination exhibiting second order nonlinear optical properties. Such a combination includes a chemically inert medium and the nonlinear optical compound of the present invention. The nonlinear optical compounds of these combinations preferably have an external field-induced molecular alignment.

In one embodiment of this aspect of the invention the nonlinear optical compound is disposed as a layer or layers on a substrate of the chemically inert medium, which chemically inert medium is selected from glass, silica, silicon and polymeric materials. In another embodiment of this aspect of the invention, the nonlinear optical compound is in the form of a blend of a guest compound in a host matrix, with the nonlinear optical compound of the present invention serving as the guest compound and the chemically inert medium serving as the host matrix, and preferably being a thermoplastic polymer selected from polyacrylates, polymethacrylates, polyacrylamides polycarbonates, polyamides, polyesters, polystyrenes, polyimides, polyether ketones, polyether etherketones, polyphenylene ethers and copolymers thereof.

In still another embodiment of this aspect of the present invention, pendant side chains of the nonlinear optical material of the present invention are covalently bonded to a chemically inert polymeric material so that a combination is provided corresponding to Formula II:

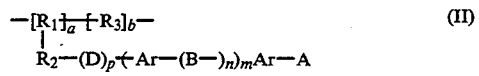
(II)

wherein $R_1$ and $R_3$ are monomeric subunits independently selected from polyacrylate, polyimide, polyamide, polyacrylamide, polystyrene, polyvinyl halide, polyacrylonitrile, polyvinyl alcohol, polyvinyl acetate, polyester, polyethylene, polypropylene, polyisobutylene, polyisoprene, poly acid anhydride, and polycarbonate monomeric subunits, wherein each $R_1$ subunit includes a functional group through which side chains may be attached;

$R_2$ is a straight-chained or branched alkyl, alkoxy, alkylthio or alkylamino group containing from one to ten carbon atoms attached to the monomeric subunit at the functional group of the subunit. The value of p is zero or one, provided that when p is zero, $R_2$ is attached to the functional group by the alkyl moiety and $R_2$ is an alkoxy, alkylthio or alkylamino group.

Ar, B, D, A, m and n are as described above; and the ratio of a to b is between about 1:99 and about 50:50. In one embodiment of this aspect of the invention, A is a tricyanovinyl electron accepting group that is attached to a heteroaromatic ring, alpha to the heteroatom of the ring. A polymeric non-linear optical compound in accordance with this embodiment has a structure represented by Formula IIA:

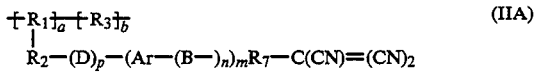
(IIA)

D, Ar, B, $R_7$, m, n, and p are the same as described above with respect to Formula IA, $R_1$, $R_2$, $R_3$ and the ratio of a to b is the same as described above with respect to Formula II. The tricyanovinyl group is substituted alpha to a heteroatom. $R_2$ or D and B are attached to a member of the heteroaromatic ring of Ar or $R_7$ alpha to a heteroatom, and when Ar is an aromatic ring, B is attached to a member of the aromatic ring para to $R_2$ or D or another B.

Another aspect of the present invention provides a method of preparing a polymer having second order non-linear optical properties. The method includes the steps of forming a reaction mixture of tetracyanoethylene and a base polymer having pendant side chains, which polymer has recurring structural units represented by Formula III:

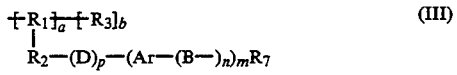
(III)

in a basic solvent at a temperature between about 0° C. and about 150° C., so that $R_7$ of the pendant side chain is tricyanovinylated; and recovering the resulting polymer having pendant tricyanovinylated side chains;

$R_1$, $R_2$, $R_3$, Ar, B, D, $R_7$, m, n and p and the ratio of a to b are the same as described above with respect to Formula IIA. $R_7$ is a five-membered heteroaromatic ring or a fused ring system containing at least one five-membered heteroaromatic ring, which heteroaromatic ring or rings have one heteroatom selected from O, N, S and Se; and $R_2$ or D and B are attached to a member of the heteroaromatic ring of Ar or $R_7$ alpha to a heteroatom, and when Ar is an aromatic ring, B is attached to a member of the aromatic ring para to $R_2$ or another B.

Another aspect of the present invention provides a base polymer having pendant side chains capable of being tricyanovinylated to form a polymer having second order non-linear optical properties. The base polymer includes recurring structural units represented by Formula III, in which $R_1$, $R_2$, $R_3$, Ar, B, D, $R_7$, m, n, p and the ratio of a to b are the same as described above with respect to Formula III.

The NLO compounds of the present invention, including the polymeric materials of the present invention, possess at least the second order NLO properties of the materials of the prior art, and in most instances demonstrate far superior second order NLO properties. Those compounds that possess equivalent second order NLO properties compared to the prior art have significantly increased solubility both in polymer matrices and in spin-casting solvents, attributable to the presence of five-membered heteroaromatic rings, making the compounds ideal candidate for NLO materials. The increase in solubility is so dramatic that it is now possible to include in polymer matrices or dissolve in spin-casting solvents compounds having three, four or even more heteroaromatic rings or ring systems. Without the presence of one or more five-membered heteroaromatic rings, the compounds would otherwise be completely insoluble. The additional five-membered heteroaromatic rings provide the compounds with superior second order NLO properties.

The presence of the five-membered heteroaromatic ring increases the extent of the electron delocalization and facilitates the enhancement of the NLO activity as the number of aromatic rings increases. On the other hand it has been found that in the absence of the five-membered heteroaromatic rings the NLO activity ceases to significantly increase when the total number of aromatic rings is more than two.

The increased second order NLO properties of the NLO compounds of the present invention is also not simply the result of increasing the number of aromatic rings. While not being bound by any particular theory, it is believed that the increased efficiency of the second order NLO properties of the heteroaromatic NLO compounds of the present invention is attributable to the higher degree of pi-delocalization possessed by a five-membered heteroaromatic ring. The use of five-membered as opposed to six-membered heteroaromatic rings also eliminates the use of ionic heteroaromatic species that cause severe current leakage during the dipole-alignment electric field poling processes.

The present invention further includes the discovery that the second order NLO properties of five-membered heteroaromatic ring compounds are significantly increased by the use of particularly strong electron donating groups such as pyrrolidine, tetrathiafulvalene and particularly strong electron accepting groups such as dicyanoethylene, tricyanoethylene, and dinitroethylene. The second order NLO properties improvement resulting from the use of strong electron donating and accepting groups with heteroaromatic compounds has been discovered to be significantly greater than the improvement resulting from the use of strong electron donating and accepting groups with compounds having only benzenoid-aromatic rings. The compounds of the present invention, in addition to their improved SHG efficiencies, are also much easier to synthesize than their non-heteroaromatic counterparts.

The present invention additionally includes the discovery that When the aromatic ring to which the electron accepting group is to be attached is a five-membered heteroaromatic ring, the strong electron accepting group tricyanoethylene can be readily attached to the heteroaromatic ring, by reacting the ring with tetracyanoethylene in a basic solvent at a given temperature. Tetracyanoethylene will not react with extended benzenoid structures under these conditions. The tricyanoethylene group is so readily attached that polymeric materials can first be synthesized from monomers having covalently bonded pendant side chains of the non-linear optical materials of the present invention having no electron accepting groups. This alleviates the solubility and reactivity problems associated with particularly strong electron accepting groups in polymerization reactions, resulting in polymers having high molecular weights and polymer yields as high as 100%.

The base polymer is then easily reacted with tetracyanoethylene in a basic solvent at a given temperature to attach the tricyanoethylene group to the pendant side chain. Full attachment of the group is possible with copolymers having up to 40% monomeric subunits with pendant side chains of non-linear optical materials.

The high molecular weight base polymer has good overall solubility and a low $T_g$. However, the $T_g$ increases upon attachment of the tricyanoethylene group although the solubility does not significantly suffer. It is possible to take advantage of the low $T_g$ of the base polymer by first forming a thin film of the base polymer and then reacting the base polymer film with tetracyanoethylene to attach tricyanoethylene groups to the polymer and produce a film having non-linear optical properties. This is particularly desirable if the difference in $T_g$ between the base polymer and polymer having non-linear optical properties result in the base polymer having significantly superior mechanical properties over the polymer having non-linear optical properties.

In addition to possessing greater second order NLO susceptibilities and improved solubility, the compounds of the present invention are thermally stable, photochemically unreactive, have high laser damage thresholds, are easily synthesized and have well-known and understood chemical properties.

DETAILED DESCRIPTION OF THE PREFERRED EMBODIMENTS

The heteroaromatic NLO compounds of the present invention, once suitably oriented, exhibit a high second order NLO susceptibility. Compounds suitable for use as second order NLO chromophore materials according to the present invention have from two to ten five-membered heteroaromatic or six-membered aromatic rings and/or fused ring systems of five- and/or six-membered aromatic or heteroaromatic rings, with one or more pi-conjugated functional groups bridged between the rings or ring systems. Within the present specification "aromatic" rings are defined as aromatic carbocyclic rings such as phenyl groups. "Heteroaromatic" rings are defined as being limited to aromatic heterocyclic rings, thereby excluding carbocyclic rings such as phenyl groups. The bridged ring compounds will thus possess the structure of Formula I.

The number of aromatic rings or fused ring systems, Ar, in a side chain, is designated as m+1, and is from two to ten, and preferably from two to four. That is, m is from one to nine, and preferably from one to three. The aromatic rings or fused ring systems within each compound may be the same or different.

At least one ring, Ar, alone, or within a fused ring system, is a five-membered heteroaromatic ring having one heteroatom selected from O, N, S and Se. The heteroaromatic ring may optionally include up to three additional N atoms. Preferably, the NLO compounds contain two or more of the five-membered heteroaromatic rings, alone or as part of a ring system. Most preferably, all the rings in the NLO compounds are five-membered heteroaromatic rings, and all ring systems contain a five-membered heteroaromatic ring. When two or more heteroaromatic rings are present, the rings may have the same or different heteroatoms.

From the foregoing description, the aromatic, heteroaromatic and fused ring systems suitable for use with the present invention can be easily identified by those of ordinary skill in the art. Suitable rings and ring systems include, but are not limited to, pyrrole, furan, thiophene, imidazole, oxazole, thiazole, triazole, tetrazole, pyrazole, pyrimidine, purine, quinolines, carbazole, benzene, naphthalene, furazan, pyrazine, indole, isoindole, indazole, phenothiazine, benzotriazole, anthracene, phenanthrene, azophenanthrenes, and the like.

The fused ring systems should not be so large as to hinder the solubility of the NLO compounds in polymer matrices or spin-casting solvents. The point at which fused ring system size interferes with solubility is easily identified by those of ordinary skill in the art. Fused ring systems of two to three rings are preferred, and two ring systems are most preferred.

The adjacent aromatic rings in each NLO compound are bridged by from one to three pi-electron conjugated functional groups such as carbon-carbon, carbon-nitrogen or nitrogen-nitrogen functional groups, depicted in the foregoing structure as B. Preferably, the adjacent aromatic rings are bridged by one or two of the conjugated functional groups. When adjacent aromatic rings are bridged by two or three functional groups, the conjugated functional groups may be the same or different and the number of conjugated functional groups between adjacent aromatic rings may vary within an NLO compound. When the aromatic ring is heteroaromatic, the functional group is substituted on the ring alpha to a heteroatom. For six-membered aromatic rings, the functional group is substituted para to another functional group, an electron donating group or an electron acceptor group.

The use of pi-electron conjugated functional groups to bridge adjacent aromatic rings in NLO compounds is essentially conventional to the art of NLO active organic materials. Examples of suitable aromatic ring-bridging functional groups known in the art include —N=N—, —CH=N—, —CH=N—N=CH—, —C≡C— and

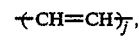

with j being from one to three.

To induce charge asymmetry, the aromatic or heteroaromatic rings at each end of the structure are substituted with an electron donating group, D, and an electron accepting or withdrawing group, A. For heteroaromatic rings, the electron donating group is substituted alpha to the heteroatom, preferably the same heteroatom that a conjugated functional group is alpha to. For rings with no heteroatoms, the electron donating group is substituted para- to the functional group bridging the ring to the ring adjacent to it.

The electron accepting groups are attached to the aromatic ring at the opposite end of the structure. As with electron donating groups, the electron accepting groups are substituted alpha to a heteroatom in heteroaromatic rings, preferably the same heteroatom that a functional group is alpha to, and on rings having no heteroatom are substituted para- to a functional group bridging the ring to a ring adjacent to it.

The electron donating and accepting groups that are used to induce charge asymmetry to the conjugated ring systems of these structures are essentially conventional to the art of NLO active organic materials. Any functional group capable of releasing electrons into such a conjugated ring system is suitable for use as an electron donating group. Examples of suitable electron donating groups known in the art include —$OR_8$, —$SR_8$, —$TeR_8$, —$SeR_8$, —CH=$NR_4$, —CH=N—$NH_2$, —CH=N—$N(R_5R_6)$ and —CH=$C[N(R_5R_6)]_2$, wherein $R_4$ is hydrogen or an alkyl group containing up to 10 carbon atoms, $R_8$ is an alkyl group containing up to 6 carbon atoms and $R_5$ and $R_6$ are independently selected from hydrogen, alkyl groups containing up to 12 carbon atoms and alkyl groups containing up to 12 carbon atoms having reactive functional groups selected from hydroxy, ethylene, acetylene, amine, thiol, sulfonic acid, carboxylic acid, or $R_5$ and $R_6$ together form a cyclic group containing up to 8 carbon atoms, including groups such as pyrrolidine, piperidine, piperazine and morpholine. Preferably, $R_3$ is a methyl group, $R_4$ is either hydrogen or a methyl group, and $R_5$ and $R_6$ are methyl, ethyl, hexyl, cyclopentyl, cyclohexyl, pyrrolidine, piperidine, piperazine and morpholine.

Another example of suitable electron donating groups are the functional groups

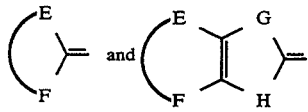

wherein E and F are members of a saturated or unsaturated five- to eight-membered cyclic ring or two ring system having five- to eight-membered rings that are electron donating in nature. E, F, G, and H are heteroatoms independently selected from O, N, S, Se and Te. Whether or not a ring is electron donating in nature to meet the definition of membership within this group is understood by those of ordinary skill in the art.

Any functional group capable of withdrawing electrons from a conjugated ring system is suitable for use as an electron accepting group. Examples of suitable electron accepting groups known in the art include —$NO_2$, —CN, —CHO, —COR, —COOR, —$PO(OR)_2$, —$SO_2R$, —$SO_3R$, —$PO(R)_2$ and

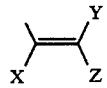

wherein X, Y and Z are independently selected from hydrogen —CN, —$NO_2$, —COR, —COOR, —$SO_2R$, —$PO(R)_2$ and —$PO(OR)_2$ and R is an alkyl group containing up to 15 carbon atoms, and preferably a methyl group.

Strong electron donating and electron accepting groups are preferred, which significantly increase the second order NLO properties of the compounds of the invention. Examples of strong electron donating groups are —$N(CH_3)_2$, pyrrolidine, piperidine, piperazine and morpholine. The most preferred strong electron donating group is pyrrolidine Examples of strong electron accepting groups are —C(CN)=$C(CN)_2$, —$NO_2$, dicyanoethylene, dinitroethylene and nitroesterethylene. The most preferred strong electron accepting group is —C(CN)=$C(CN)_2$, a tricyanoethylene or tricyanovinyl group.

When the electronic accepting group is a tricyanovinyl group, the non-linear optical compounds of the present invention preferably have a structure represented by Formula IA, in which D, Ar, B, $R_7$, m and n are the same as described above with respect to Formula IA. As noted above, the tricyanovinyl group is substituted alpha to the heteroatom.

A preferred embodiment of the present invention includes a second electron donating group substituted alpha to the electron donating group on the aromatic ring at one end of the structure, or a second electron accepting group alpha to the electron accepting group on the aromatic ring at the opposite end of the structure, or both. The second electron donating or accepting group may be the same or different than the corresponding first electron donating or accepting group. The inclusion of a second electron donating or electron accepting group in the alpha position increases the second order NLO properties of the resulting material as compared to materials having single-substitution of electron donating and electron accepting groups.

The aromatic rings of the NLO compounds of the present invention may optionally be further substituted. Any number of functional groups can be substituted on the rings, provided that the groups are not so large or so numerous to cause undesirable steric hindrance effects, the occurrence of which will be clear to those of ordinary skill in the art.

General procedures for the preparation of the NLO compounds of the present invention are illustrated by the following Schemes.

NLO compounds having —CH=CH— (stilbene) functional groups are prepared by a Wittig reaction. The Wittig reaction can be performed by the reaction of a phosphonium salt or phosphonate ester with an aldehyde in the presence of a base. The Wittig condensation reaction is illustrated in Scheme 1:

Scheme 1

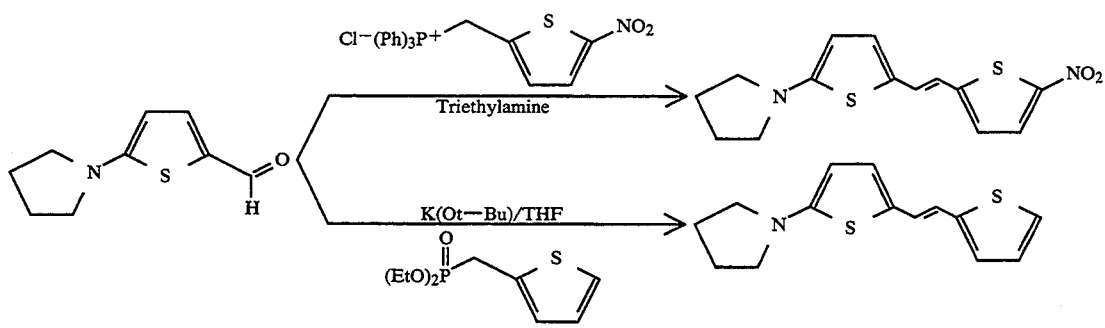

NLO compounds having —C≡C— (acetylene) bridges are prepared from stilbene type compounds by conventional methods. The stilbene is brominated and subsequently dehydrobrominated to yield the desired acetylene. The preparation of acetylene compounds is illustrated in Scheme 2.

Scheme 2

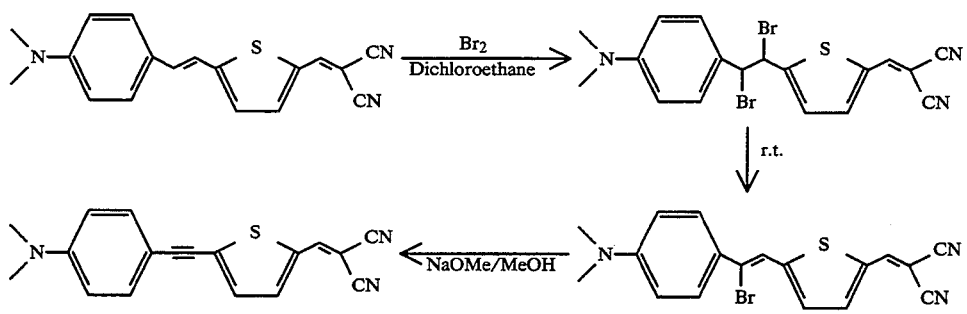

NLO compounds having —CH=N— (azine or schiff base) functional groups are prepared by refluxing an aromatic amine with the appropriate aldehyde or ketone in alcoholic solvents. The reaction times and temperatures vary with the substituents present on both the carbonyls and amines. A general procedure employed to synthesize schiff base materials is illustrated in Scheme 3:

Scheme 3

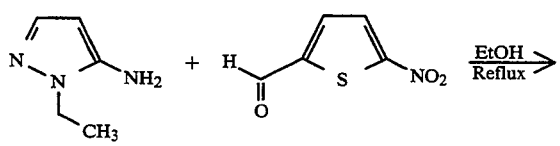

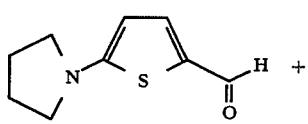

-continued
Scheme 3

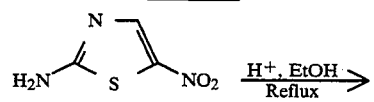

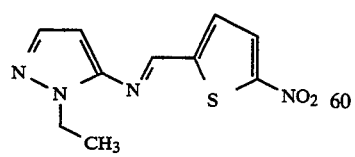

NLO compounds having —CH=N—N=CH— (azine) functional groups are prepared by the condensation of aromatic electron deficient aldehydes with hydrazine and the resulting hydrazone is condensed with an electron rich aldehyde. The hydrazine condensation is illustrated in Scheme 4.

Scheme 4

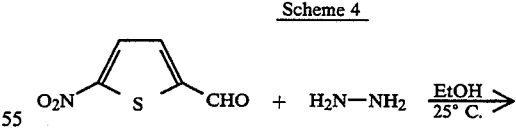

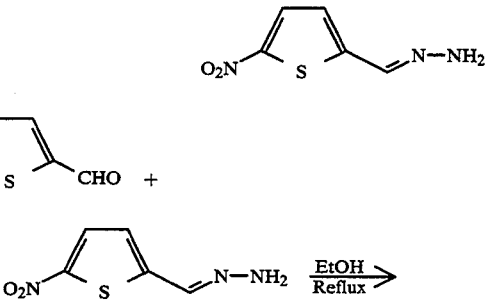

-continued
Scheme 4

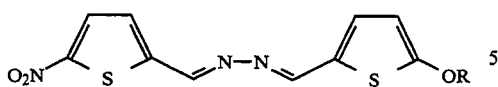

NLO compounds having —N=N— (azo) functional groups are prepared by conventional azo coupling reactions in which an aromatic ring substituted with a powerful electron donating group such as —N(CH$_3$)$_2$, is reacted with an aromatic diazonium salt in mildly acidic solution. The azo coupling is illustrated in Scheme 5:

Scheme 5

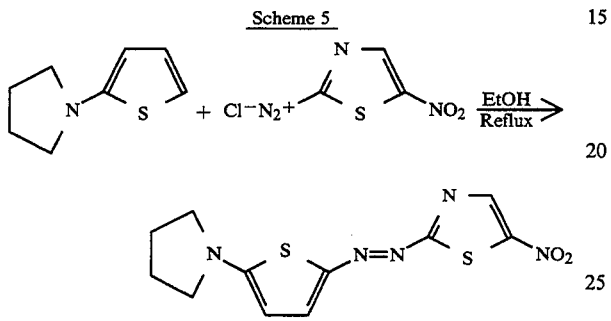

NLO compounds having —CH=CH—CH=CH— (diene) bridges are prepared by a variety of ways. One such way is by a Wittig reaction with a conjugated aldehyde. This type of Wittig reaction is illustrated by Scheme 6.

Scheme 6

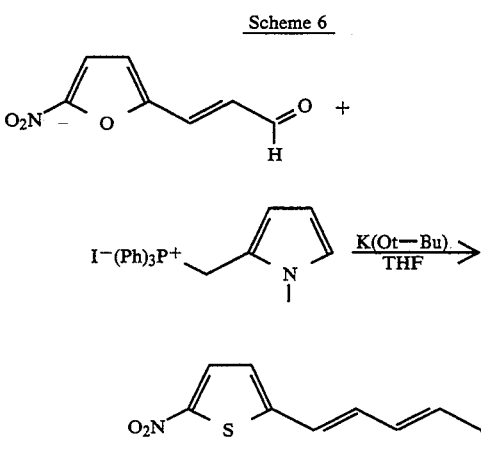

The synthesis of bridges is one important aspect of the NLO material. Another aspect is the extension of the conjugation. In the synthesis of these heterocyclic NLO materials, there are two separate ways of extending the conjugation: 1) sequential build-up of rings or 2) addition of multiple rings in one step, illustrated in Scheme 7:

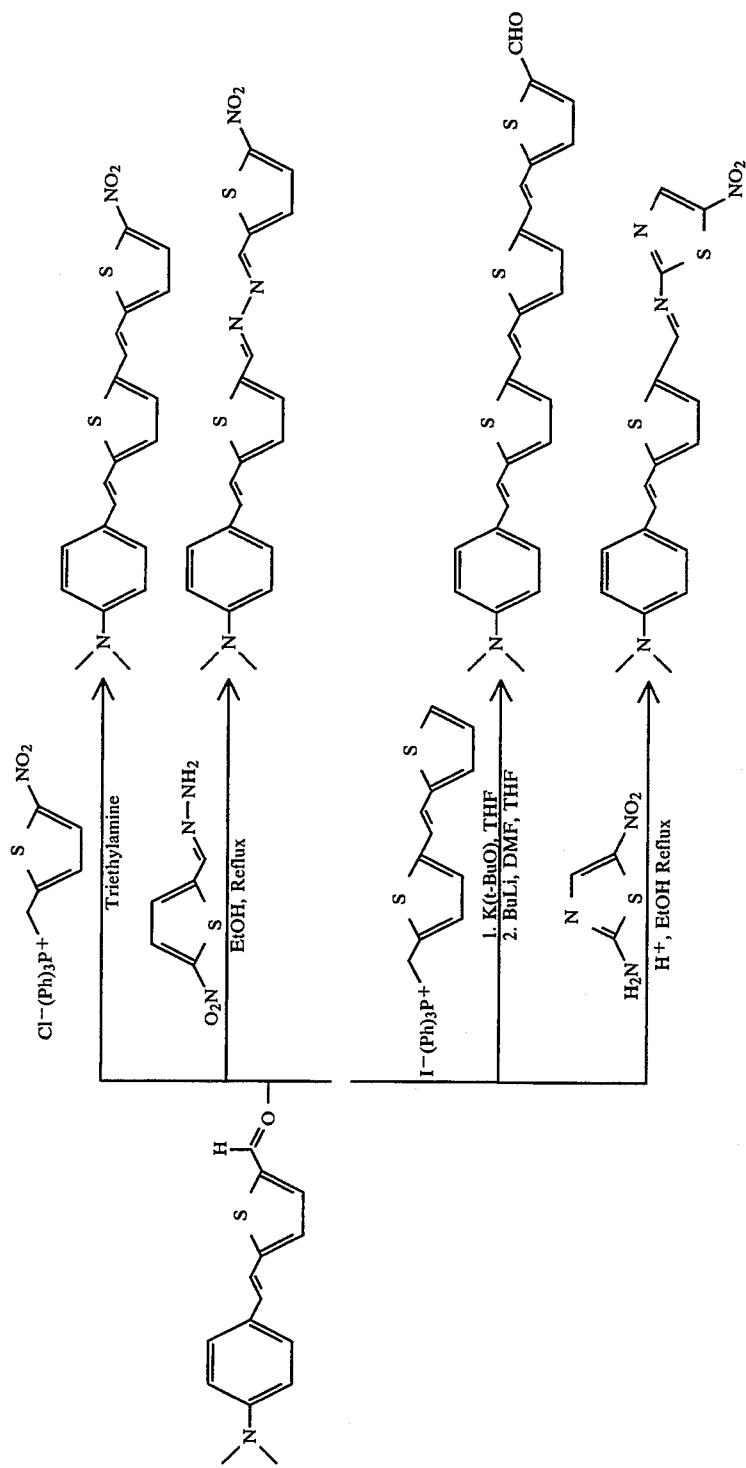

A variety of electron acceptor groups such as tricyanoethylene, dicyanoethylene, cyanoesterethylene, etc., can be substituted to the heteroaromatic or aromatic ring using conventional methods. While the methods may be conventional, it has unexpectedly been discovered that the tricyanoethylene electron acceptor group can be directly attached to a heteroaromatic ring, a reaction that does not readily occur with benzene rings.

Any of the aromatic rings, electron donating groups or electron accepting groups disclosed as being suitable for use with the present invention may be substituted for the aromatic rings, electron donating groups or electron accepting groups depicted in the foregoing schemes without undue experimentation. The foregoing procedures can be combined sequentially to provide NLO materials combining various five- or six-membered aromatic rings bridged by one or more of the same or different stilbene, schiff base, azomethine, azo, acetylene or alkene functional groups.

The NLO compounds of the present invention can be formed into a nonlinear optical material by combining the NLO compounds with a chemically inert medium. For example, the NLO compounds can be layered on a substrate such as glass, silica or polymeric materials, as described in U.S. Pat. No. 4,894,186 to Gordon, the disclosure of which is hereby incorporated herein by reference thereto. In another embodiment, a nonlinear optical medium can be formed by blending the NLO compounds of the present invention with a host thermoplastic polymer. Suitable host thermoplastic polymers include polyacrylates, polymethacrylates, polyacrylamides, polyimides, polycarbonates, polyesters, polyamides, polystyrenes and the like. This combination is also described in U.S. Pat. No. 4,894,186, the disclosure of which is also hereby incorporated herein by reference thereto.

The NLO compounds of the present invention can also be covalently attached as side chains to the monomeric subunits of polymers. Polymers should be chosen for use with the present invention having monomeric subunits that have reactive functional groups for attachment of the side chains.

The polymer should also have excellent optical transparency, good film-forming characteristics, a low dielectric constant and a relatively high $T_g$ for stable dipole orientation of the side chains. Other properties will come into consideration, depending upon the particular end use requirements of the materials; however, these properties are well understood by those of ordinary skill in the art.

One class of polymers suitable for use with the present invention are polymers and copolymers, the monomeric subunits of which are derived from vinyl monomers such as acrylates, acrylamides, vinyl halides, acrylonitriles, ethylene, propylene, isobutylene, isoprene, acid anhydrides, styrenes, vinyl alcohols and vinyl acetates. Examples of other polymers suitable for use with the present invention include polyimides, polyamides, polycarbonates, polyesters, polyphenylene ethers, polyetherimides, polyether ketones and polyether etherketones.

The polyacrylates suitable for use with the present invention include alkyl branched polyacrylates such as polymethyl methacrylate. Likewise, the polyacrylamides suitable for use with the present invention include alkyl branched polyacrylamides such as polymethacrylamide, and the polyacrylonitriles include alkyl branched polyacrylonitriles such as polymethacrylonitrile.

Those of ordinary skill in the art are capable of identifying the functional groups of the polyacrylates, polyimides, polyamides, polyacrylamides, polyvinylhalides, polyacrylonitriles, polyvinyl alcohol, polyvinyl acetates, polyesters, polyphenylene ethers, polyetherimides, polyether ketones, polyether etherketones, poly (acid anhydrides) and polycarbonates to which the NLO compounds of the present invention can be attached to form side chains by conventional addition and condensation reactions. Although the monomeric subunits of polystyrene, polyethylene, polypropylene, polyisobutylene and polyisoprene do not have such functional groups, such monomeric subunits can first be functionalized to provide a reactive group for the attachment of the NLO compound, such as the chloromethylation of polystyrene and the subsequent conversion to the more reactive iodomethyl derivative set forth in U.S. Pat. No. 4,935,292 to Marks, the disclosure of which is herein incorporated by reference thereto. Alternatively, a functionalized derivative of these polymers can be used as a starting material, such as the poly(p-hydroxystyrene), the use of which is also disclosed by U.S. Pat. No. 4,935,292.

Attachment of the NLO compounds to the monomeric subunits results in a polymer having side chains corresponding to Formula II, wherein $R_1$ and $R_3$ represent the monomeric subunits of the above-described polymers, which may be the same or different, D, Ar, B and A are as described above with respect to Formula I, $R_2$ is a straight-chained or branched alkyl, alkoxy, thioalkyl or aminoalkyl group containing from one to ten carbon atoms, n is from one to three, m is from one to nine, and p is zero or one. When p is zero, $R_2$ is attached to the functional group by the alkyl moiety and $R_2$ is an alkoxy, alkylthio or alkylamino group. The ratio of a to b represents the degree to which the monomeric subunits of the polymer are substituted by NLO side chains. In the present invention, the ratio of a to b is between about 1:99 and about 50:50. Preferably, the ratio of a to b is between about 5:95 and about 40:60 and most preferably, it is about 25:75. The ratio of a to b should not substantially exceed 30:70 in order that the polymer remains soluble in solvents utilized in the preparation of NLO materials.

$R_2$ functions to attach the NLO compounds to the functional groups of the monomeric subunits of the polymers to form NLO side chains. While $R_2$ is a straight-chained or branched alkyl, alkoxy, thioalkyl or aminoalkyl group containing from one to ten carbon atoms, preferably, $R_2$ will contain from four to six carbon atoms. More preferably, $R_2$ is selected from $(-CH_2)_x$, $(-CH_2-R_9-)_x$, $(-CH_2-CH_2-R_9-)_{x/2}$, $(-CH_2-CH_2CH_2-R_9-)_{x/3}$, wherein $R_9$ is selected from O, S and NH and x is from one to ten, preferably from four to six, with the proviso that for $(-CH_2-CH_2-R_9-)$, x is a multiple of two, and for $(-CH_2-CH_2-CH_2-R_9-)$, x is a multiple of three. $R_2$ additionally functions to increase the solubility of the polymer in the chemically inert medium or solvents utilized.

Preferred NLO polymers have recurring structural units represented by Formula IIA wherein $R_1$, $R_2$, $R_3$, Ar, B, D, $R_7$, m, n and p are the same as described above with respect to Formula IIA. The tricyanovinyl group is attached alpha to the heteroatom of $R_7$. The a to b monomer ratio is the same as described above with respect to Formula II. In even more preferred polymers, $R_1$ and $R_3$ are independently selected from monomers of ethylene, acrylates, alkyl-branched acrylates, acrylamides, alkyl-branched acrylamides, styrene, alpha-alkyl styrenes, vinyl acetate, ether ketones and ether etherketones. When $R_1$ or $R_3$ is a styrene monomer, the aromatic ring may be further substituted by one or more hydroxyl or alkyl groups, provided that the groups are not so large or so numerous to cause undesirable steric hindrance effects, the occurrence of which will be clear to those of ordinary skill in the art.

In the most preferred NLO polymers, $R_1$ and $R_3$ are independently selected from monomers of acrylates, methacrylates, etherketones and ether etherketones.

The base polymers of the present invention have recurring structural units corresponding to the recurring structural units of the NLO polymers of the present invention, but without the electron accepting groups. Therefore, base polymers in accordance with the present invention have recurring structural units represented by Formula III, in which $R_1$, $R_2$, $R_3$, Ar, B, D, $R_7$ m, n and p are the same as described above with respect to Formula III. $R_1$ and $R_3$ may be the same or different, as described above with respect to the NLO polymers of Formula IIA with the same a to b monomer ratio as described above with respect to Formula IIA. As with the polymers of Formula IIA, in even more preferred base polymers, $R_1$ and $R_3$ are independently selected from monomers of ethylene, acrylate, alkyl-branched acrylates, acrylamides, alkyl-branched acrylamides, styrene, alpha-alkyl styrenes, vinyl acetate, ether ketones and ether etherketones. $R_1$ and $R_3$ for the most preferred base polymers are independently selected from monomers of acrylates, methacrylates, ether ketones and ether etherketones.

The polymerization of the base polymers and polymeric NLO materials of the present invention is essentially conventional and is readily understood by those of ordinary skill in the art. Depending upon the material in question, in some cases it is preferable to first polymerize the polymer and then attach the side chains to the functional groups, in other cases it is preferable to synthesize a monomer having a NLO side chain covalently attached there to be copolymerized with monomer having no side chain.

A preferred method for the preparation of the polymeric NLO materials of the present invention, however, first synthesizes a monomer having a pre-NLO side chain covalently attached thereto. The pre-NLO side chain is defined as an NLO side chain having no electron accepting group. Once the monomer having a pre-NLO side chain is copolymerized with a monomer having no NLO or pre-NLO side chain, the resulting base polymer can be reacted to attach electron accepting groups to the pre-NLO side chains to provide a polymeric NLO material. The synthesis of monomers having pre-NLO side chains and the copolymerization of same with a monomer having no NLO or pre-NLO side chains is essentially conventional and well-understood by those of ordinary skill in the art. The base copolymer is then preferably reacted with tetracyanoethylene to tricyanovinylate the pre-NLO side chains. The base polymer can be reacted with tetracyanoethylene in a basic solvent at an elevated temperature to achieve such tricyanovinylation.

For polymers having monomeric subunits such as acid anhydrides, epoxides, acid halides, isocyanates, carboxylic acids, esters, sulfonic acids and amines, the pre-NLO side chain can be directly attached to the polymer, rather than first synthesizing a monomer having a pre-NLO side chain that is then polymerized with an unsubstituted monomer to form a pre-NLO base polymer. The base polymer can instead be reacted to attach electron accepting groups such as tricyanovinyl groups to the pre-NLO side chains to provide a polymeric NLO material. For example, pre-NLO side chains can be reacted with poly(styrene maleic anhydride) to form a poly(styrene maleimide) having pre-NLO side chains. The method by which pre-NLO side chains can be directly attached to polymers is also essentially conventional and well-understood by those of ordinary skill in the art.

Suitable basic solvents for the reaction of tetracyanoethylene and the base polymer include N,N-dimethylformamide (DMF), pyridine, N,N-dimethylacetamide, N-methyl pyrrolidone, tertiary amines and the like. The preferred solvent is DMF. A reaction mixture is prepared by dissolving the polymer and the tetracyanoethylene in one or more of the above solvents. The reaction mixture is heated to a temperature between about 50° C. and about 140° C., and preferably about 100° C. to obtain the tricyanovinylated polymers.

The degree of tricyanovinylation of the polymer is limited only by the number of pendant pre-NLO groups available for tricyanovinylation. Therefore, a slight equivalent excess of the tetracyanoethylene over the polymer should be used.

As noted above, the reaction of the polymer and the tetracyanoethylene can be carried out at temperatures in the range of from about 50° C. to about 140° C. Higher temperatures will result in an increased rate of reaction. And even higher rates can be achieved by pressurizing the reaction vessel to elevate the boiling point of the solvent, allowing the reaction to proceed at an even higher temperature. However, a reaction temperature of 100° C. is preferred to minimize inter- and intra-molecular cross reactions.

To insure uniform mixing of the polymer and the tetracyanoethylene, the reaction mixture should be maintained at a constant state of mild agitation. It is also preferred that the reaction mixture be maintained under an atmosphere of an inert gas.

Once the reaction is complete, the NLO polymer is precipitated with a lower alkyl alcohol, such as methanol or isopropanol, filtered and dried under vacuum. The polymer can then be further purified by conventional methods, typically by repeated dissolution and reprecipitation from the lower alkyl alcohol.

One key intermediate in the preparation of vinylic monomers such as an acrylate, with NLO side chains is 4-[(6-hydroxyhexyl) methylamino] benzaldehyde, the preparation of which is essentially conventional. Five-membered heterocyclic and/or six-membered aromatic aldehydes can be Substituted for this compound for preparation of the other NLO side chains of the present invention.

A general procedure employed to synthesize acrylate monomers with stilbene type side chains, followed by copolymerization with unsubstituted acrylate monomer, is illustrated in Scheme 8:

Scheme 8
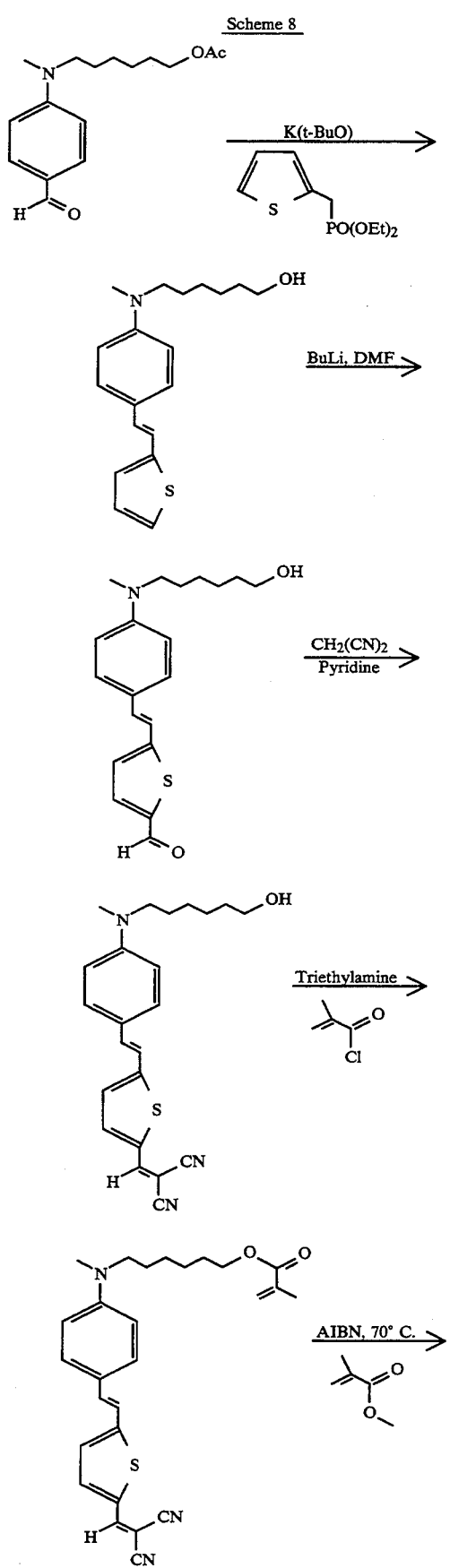
-continued
Scheme 8
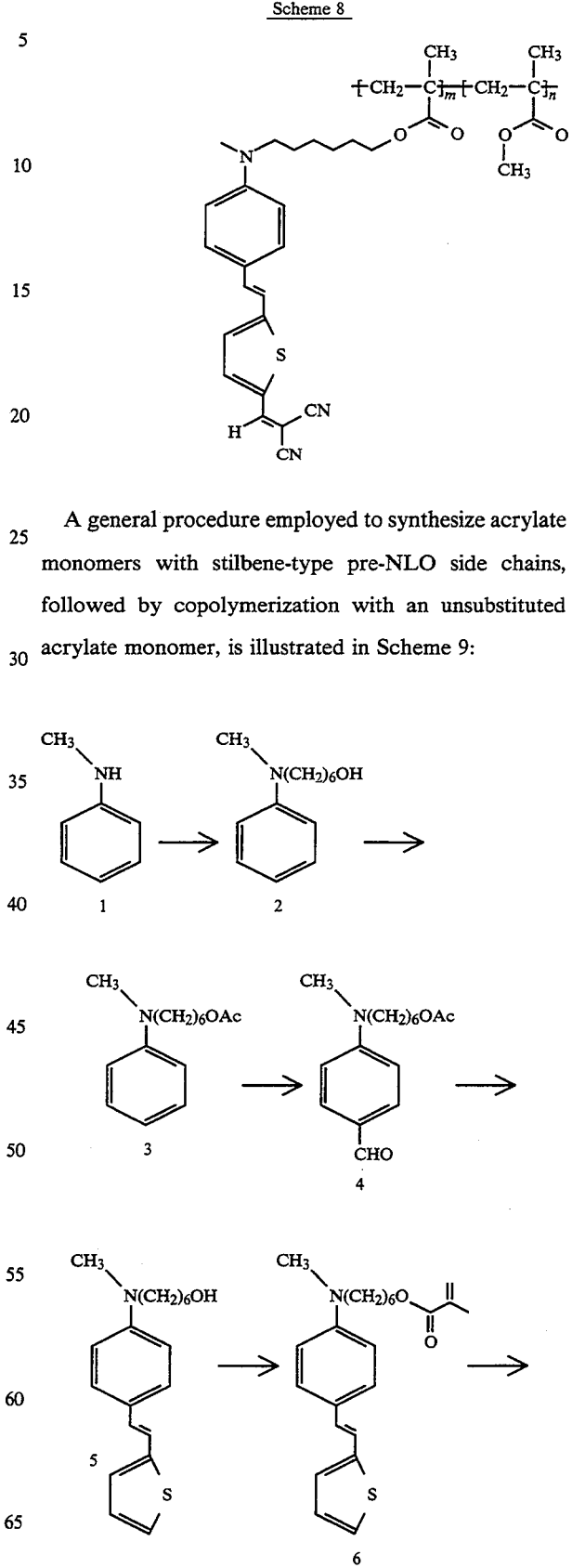
A general procedure employed to synthesize acrylate monomers with stilbene-type pre-NLO side chains, followed by copolymerization with an unsubstituted acrylate monomer, is illustrated in Scheme 9:

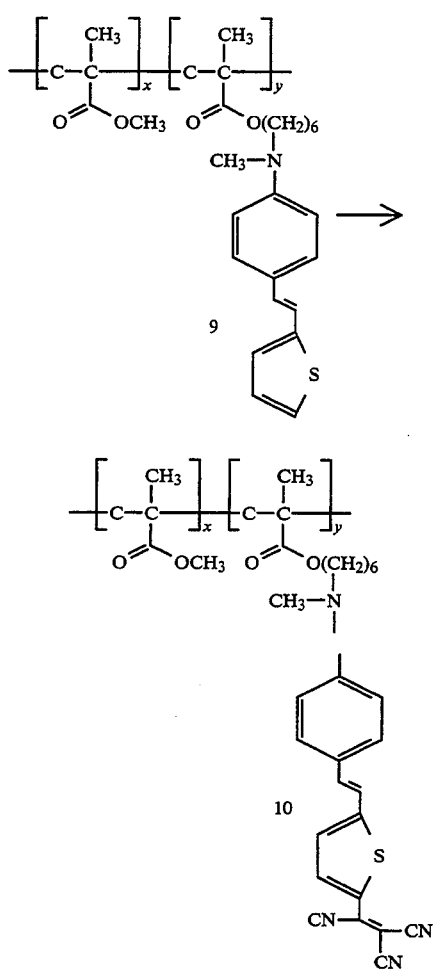

The foregoing reactions can also be employed with a Schiff base, azomethine, azine, azo, acetylene or alkene functional group NLO compounds by using hydroxyalkyl-substituted starting materials.

The polymeric materials having NLO active side chains are recovered and purified by conventional means known to those of ordinary skill in the art. Films of the polymers may be formed by spin coating, after which the films may be repetitively annealed prior to poling at an elevated temperature near the $T_g$ of the material. Following annealing, the dipoles of the side chains may be aligned by application of an intense electric field (0.2–1.0 MV cm$^{-1}$) at temperatures near the $T_g$. The foregoing sequence of spin coating, annealing and poling is essentially conventional and disclosed in U.S. Pat. No. 4,935,292, the disclosure of which is hereby incorporated herein by reference thereto.

It is disclosed in U.S. Pat. No. 4,935,292 and SPIE Proceeding No. 1147, 74–83 (1989) that further stabilization of the NLO side chain alignment can be achieved by a radiation-induced or chemical-induced cross-linking of the polymer matrix. This process is also essentially conventional, the disclosure of which in U.S. Pat. No. 4,935,292 is also hereby incorporated herein by reference thereto.

The preferred base polymers and NLO-active polymeric materials of the present invention typically have weight-average molecular weights between about 5,000 and about 300,000 Daltons measured by GPC or light scattering. The incorporation of the tricyanovinyl group increases the Tg's of the precursor polymers.

The electro-optic coefficient of an NLO-active poled polymer film is proportional to the product of the molecular second order nonlinear optical susceptibility coefficient, beta and the molecular ground state electric dipole moment, mu. The molecular beta is dependant on the frequency at which the measurement is performed due to the resonance effect near the absorption peak. A method to compare molecules with different absorbtion properties by extrapolation of the beta value measured at a specific frequency to zero frequency using a two-level model is disclosed by Singer, J. Opt. Soc. Am., B6, 1339–1350 (1989). The beta value at the extrapolated zero frequency is defined beta zero. The NLO active molecules of the present invention can exhibit values of the beta-mu product as high as about 15,000 in units of $10^{-48}$ esu measured at a wavelength of 1540 nm. The corresponding value of the product of beta-zero-mu is about 6000 in units of $10^{-48}$ esu.

Thus, it can be appreciated that the present invention provides NLO compounds combining superior second order nonlinear optical properties with the physical, mechanical and optical properties required of an optical material. The following examples are further illustrative of the present invention, and are not to be construed as limiting the scope thereof. The reference numerals refer to the steps of reaction schemes. Unless otherwise indicated, materials were obtained from Aldrich Chemical Supply. All parts and percentages are by weight unless expressly indicated to be otherwise.

EXAMPLES

Example 1

N-(6-hydroxyhexyl)-N-methylaniline 2 was prepared by mixing N-methylaniline (153 g, 1.43 mol.), 6-chlorohexanol (200 g, 1.46 mol.), potassium carbonate (200 g, 1.45 mol.) and potassium iodide (6 g, catalyst) in 750 mL of n-butanol. The mixture was heated to reflux under argon with vigorous external stirring for 96 hours. The solution was cooled, filtered, and the solvent was removed in vacuo. The residue was distilled under high vacuum to yield 2 (235 g, 79.5% yield) as a colorless oil, having a boiling point of 120°–125° C. (0.05 mm Hg).

Example 2

N-(6-acetoxyhexyl)-n-methylaniline 3 was prepared by heating a mixture of 2 of Example 1 (235 g, 1.13 mol.) and acetic anhydride (126 g, 1.24 mol.) in pyridine (97 g, 1.24 mol.) to reflux with stirring under argon for two hours . After cooling, the solution was poured into ice water with vigorous stirring and subsequently extracted with ethyl acetate (2×300 mL). The combined extracts were dried (Na$_2$SO$_4$), and the solvent was removed in vacuo. The residue was distilled to yield 3 (246 g, 89% yield) as a tan-colored oil having a boiling point of 145°–147° C. (0.15 mm Hg).

Example 3

4'-[(6-acetoxyhexyl) methylamino] benzaldehyde 4 was prepared by first adding phosphorous oxychloride (140 g, 0.92 mol.) dropwise to 270 mL of N,N'-dimethylformamide (DMF), with the resulting mixture being stirred for two hours at 0° C. To this mixture was added dropwise 50 mL of 3 of Example 2 (221 g, 0.91 mol.). The resulting mixture was heated to 90° C. for three hours. After cooling, the solution was poured onto 1 L of ice water and the resulting material was hydrolyzed with potassium carbonate overnight. The basic mixture was extracted with dichloromethane (3×200 mL). The organic layers were combined, dried (Na₂SO₄), and the solvent was removed in vacuo to yield a brown residue which was distilled using a short-path Kugelrohr apparatus to yield 4 (195 g, 78% yield) as a yellow oil having a boiling point of 201° C. (0.15 mm Hg).

Example 4

(Trans)-7-[4-(1-)((6'-hydroxyhexyl) methylamino benzene))] ethenyl thiophene 5 was prepared by adding potassium t-butoxide (13 g, 0.117 mol.) to a stirred solution of 4 of Example 3 (32 g, 0.115 mol.), and ethyl thiophene phosphonate ester (27 g, 0.117 mol.) in 150 mL of dry, freshly distilled tetrahydrofuran under argon at room temperature. Ethyl thiophene phosphonate ester was prepared by reacting 2-hydroxymethyl thiophene with thionyl chloride to form 2-chloromethyl thiophene. The 2-chloromethyl thiophene was then reacted with triethylphosphite at 140° C. for 8 hours to form the ethyl thiophene phosphonate ester. The reaction was essentially quantitative under this condition.

The reaction mixture of 4 and ethyl thiophene phosphonate ester was stirred in the absence of light for three hours. After this initial period, additional potassium t-butoxide (13 g, 0.117 mol.) was added to hydrolyze the acetate linkage. The resulting solution was stirred overnight under argon. The mixture was concentrated in vacuo, and the residue was dissolved in dichloromethane, washed with water (3×200 mL), dried (Na₂SO₄), and concentrated onto 30 g of silica. The silica was added to a medium pressure column packed with silica. The column was eluted with a 1:1 ratio blend of hexane and dichloromethane with a gradient to pure dichloromethane to obtain 5 (30 g, 83% yield) as a pale, yellow solid.

Example 5

(Trans)-7-[4-(1-)(6'-methacryloxyhexyl) methylamino benzene))] ethenyl thiophene 6 was prepared by cooling to 0° C. a mixture of the thiophene stilbenoid 5 of Example 4 (20 g, 63.4 mmol.) and triethylamine (6.74 g, 66.6 mmol.) in 300 mL of dry dichloromethane. The mixture was treated under argon with a solution of freshly distilled methacryloyl chloride (7.3 g, 69.7 mmol.) in 100 mL of dichloromethane. The reaction mixture was stirred at 0° C. for 2 hours and then room temperature for 48 hours. After washing with saturated sodium bicarbonate (2×200 mL), the solution was dried (Na₂SO₄) and the solvent was removed in vacuo. The resulting oil was redissolved in a minimum amount of dichloromethane and eluted with a 1:1 ratio blend of hexane and dichloromethane on a medium pressure silica column to yield 6 (19.1 g, 79% yield) as a pale, yellow oil that solidified upon cooling in the freezer.

Example 6

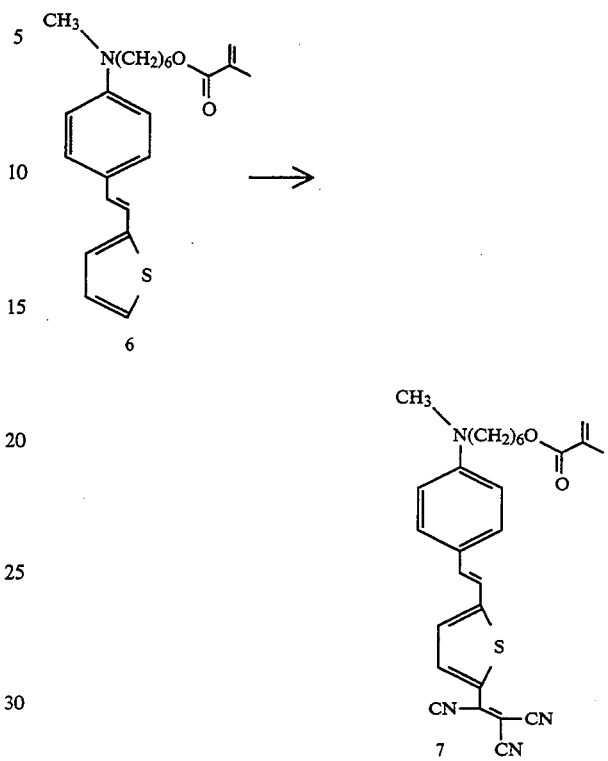

(Trans)-7-[4-(1-)(6'-methacryloxyhexyl) methylamino benzene))] ethenyl-10-tricyanovinyl thiophene 7 was prepared by gradually adding (approx. 5–10 min.) tetracyanoethylene (3.25 g, 25.37 mmol.) to a stirred solution of methacrylate 6 of Example 5 (9.91 g, 25.23 mmol.) in dimethylformamide (25 mL) at room temperature under argon. The reaction mixture was warmed to 70° C. for 2 hours. Upon cooling, the reaction mixture was poured into water (150 mL) and extracted with dichloromethane (2×200 mL). The organic layer was washed with water (3×300 mL), dried (Na₂SO₄), concentrated in vacuo and eluted with dichloromethane on a medium pressure silica column to yield 7 (12.47 g, 99% yield) as a dark black solid.

Examples 7–10

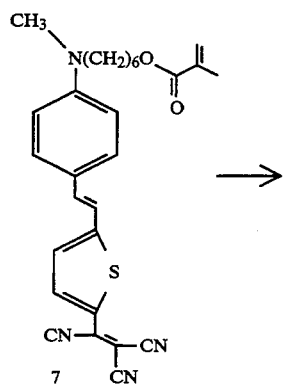

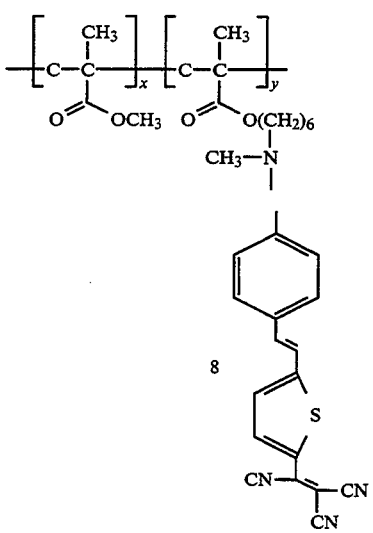

Methylacrylate monomer having tricyanovinylated NLO side chains was polymerized to form an NLO polymer by first mixing the tricyanovinylthiophene 7 of Example 6, freshly distilled methylacrylate and 2,2'-azobis-(2-methylpropionitrile) (AIBN) free radical initiator in distilled toluene (5 mL). The combined molar quantity of the two monomers was 6.25 mmol. The molar ratios of the two monomers were varied in order to vary the ratios of the monomeric repeating units in the resulting copolymers, the molar ratios of which corresponded quantitatively to the molar ratios of the monomers. The mole fraction of NLO-monomer in the polymer was determined by $^1$H-NMR. The molar ratios of monomers used and the resulting mole fractions of NLO-monomer in the polymers synthesized are shown in Table I. The mole percent concentration of free radical initiator ranged from 2.5 to 5 mmol. percent, as also shown in Table I.

The mixtures were degassed and then heated in stoppered tubes under argon at 80° C. for 48 hours. The resulting solutions were poured into 50 mL quantities of swiftly stirred methanol to precipitate the polymers as amorphorus black solids. The polymers were purified by repeated re-precipitation from dichloromethane into methanol and dried in vacuo (30 millitorr) at 65° C. for 24 hours. Molecular weights were estimated by gel permeation chromatography (GPC) in tetrahydrofuran using poly(methyl methacrylate) standards. Thermal properties were determined by differential scanning calorimetry (DSC). X represents the mole fraction of unsubstituted monomer in the polymer and Y represents the mole fraction of NLO-monomer in the polymer.

TABLE I

| Example | X | Y | Yield | MW | Initiator[a] | $T_g$ |
|---|---|---|---|---|---|---|
| 7 | 98 | 2 | 54.8 | 7000 | 5 | 108° C. |
| 8 | 78 | 22 | 60.0 | 5000 | 5 | 98° C. |
| 9 | 86 | 14 | 23.4 | 5000 | 5 | 111° C. |
| 10 | 0 | 100 | 3 | <1000[b] | 2.5 | — |

[a]Mole-percent of initiator
[b]Distribution was very broad with significant low molecular weight tail.

The data in Table I illustrates the problematic synthesis of polymers having polar side groups such as chromophores possessing a high degree of charge asymmetry, resulting in low yields of polymers having low broad molecular weight, low Tg's and low chromophore incorporation.

Examples 11-18

In the alternative, the non-tricyanovinylated monomer 6 of Example 5 was copolymerized with methyl methacrylate and then tricyanovinylated according to the procedure of Examples 7-10. Mixtures were prepared of the methacrylate 6, freshly distilled methyl acrylate and AIBN in 5 mL distilled toluene. The mole fractions of monomer and molar concentration of free radical initiator are depicted in Table II, essentially as depicted in Table I. Polymer yields and molecular weights were significantly higher, and $T_g$ increased as the degree of side-chain substitution increased.

TABLE II

| Example | X | Y | Yield | MW | Initiator[a] | $T_g^c$ | $T_g^d$ |
|---|---|---|---|---|---|---|---|
| 11 | 89 | 11 | 17 | 20,000 | 0.75 | 110° C. | 114° C. |
| 12 | 97 | 3 | 95 | 122,000 | 0.75 | 117° C. | 116° C. |
| 13 | 94 | 6 | 85 | 86,000 | 0.75 | 101° C. | 106° C. |
| 14 | 88 | 12 | 62 | 67,000 | 0.75 | 91° C. | 112° C. |
| 15 | 81 | 19 | 47 | 57,000 | 0.75 | 90° C. | 115° C. |
| 16 | 79 | 21 | 27 | 40,000 | 0.75 | 78° C. | 120° C. |
| 17 | 64 | 36 | 20 | 13,000 | 0.75 | 55° C. | 146° C. |
| 18 | 0 | 100 | 7.5 | 8,000 | 0.75 | −73° C. | — |

[a]Mole-percent of initiator.
[c]$T_g$ of non-tricyanovinylated polymer as determined by DSC.
[d]$T_g$ of tricyanovinylated polymer as determined by DSC.

Examples 19-25

The polymers of Examples 11-17 were then tricyanovinylated. Solutions of the polymers of Examples 11-17 (100 mg) in dimethylformamide (2 mL) were prepared. To these solutions, tetracyanoethylene (20 mg, excess) was gradually added (approx. 5-10 min.), with stirring, at room temperature under argon. The reaction mixtures were warmed to 110° C. for 6 hours. Upon cooling, the reaction mixtures were poured into 50 mL quantities of agitated water to precipitate the polymers as amorphous black solids. (Yields were quantitative.) The polymers were purified by repeated re-precipitation from dichloromethane into methanol, and were dried in vacuo (30 millitorr Hg) at 65° C. for 48 hours. The molecular weight and thermal properties of the tricyanovinylated polymers are shown in Table II.

Table II depicts increasing $T_g$ of the pre-NLO polymers upon tricyanovinylation. The foregoing examples also illustrate that pre-NLO monomers that are first polymerized and then tricyanovinylated provide NLO polymers in significantly higher yields with significantly higher molecular weights and thermal properties than polymers derived from monomers that are first tricyanovinylated and then polymerized.

Example 26

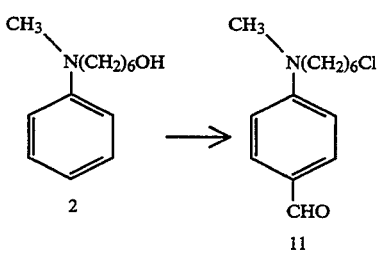

[(6'chlorohexyl) methylamino] benzaldehyde 11 was synthesized by adding phosphorous oxychloride (158 g, 1.03 mol.) dropwise at 0° C. to 150 mL of N,N'-dimethylformamide and stirring the resulting mixture at 0° C. for 2 hours. N-(6-hydroxyhexyl)-N-methylaniline 2 of Example 1 (100 g, 0.512 mol.) was added slowly, and the reaction mixture was heated to 90° C. for 3 hours. After cooling, the solution was poured onto 1 kg of ice and the resulting material was hydrolyzed with potassium carbonate. The basic mixture was extracted with dichloromethane (3×200 mL), and the organic layers were combined, dried (Na₂SO₄), and the solvent was removed in vacuo. The residue was eluted with a blend of hexane and dichloromethane on a gradient beginning with a 5:1 ratio to a 1:1 ratio blend to yield 11 (110 g, 85% yield) as a colorless oil.

Example 27

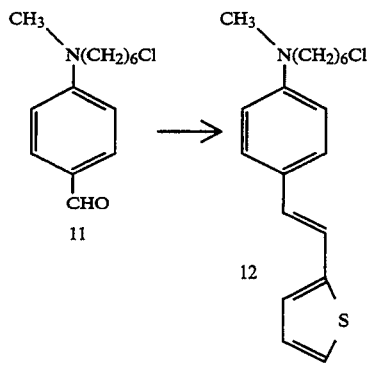

(Trans)-7-[4-(1-)(6'-chlorohexyl) methylamino benzene))] ethenyl thiophene 12 was prepared by adding a solution of the chloroaldehyde 11 of Example 26 (25 g, 100 mmol.) in 100 mL of dry tetrahydrofuran to a stirred solution of ethyl thiophene phosphonate ester (25 g, 98.2 mol.) and potassium t-butoxide (13 g, 0.117 mol.) in 300 mL of dry, freshly distilled tetrahydrofuran. The solution was warmed to 50° C. for 6 hours under argon, cooled and then concentrated in vacuo. The residue was dissolved in dichloromethane, washed with water (3×200 mL), dried (Na₂SO₄), and concentrated onto 30 g of silica. This silica was added to a medium pressure silica column. The column was eluted with a blend of hexane and dichlormethane on a gradient from a 10:1 ratio blend to a 1:1 ratio blend to yield 12 (29.4 g, 90% yield) as a pale, yellow solid.

Example 28

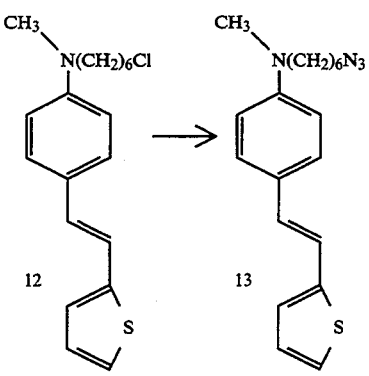

(Trans)-7-[4-(1-((6'-azohexyl) methylamino benzene))] ethenyl thiophene 13 was synthesized by suspending sodium azide (2.9 g, 44.61 mmol.) in a solution of dimethylformamide containing the chloride 12 of Example 27 (10.0 g, 29.9 mmol.). The suspension was heated to 100° C. under argon and then water was added until everything was in solution. The reaction was maintained at 100° C. for 3 hours. After cooling, the solution was poured into water (1 L) and the resulting mixture was extracted with dichloromethane (2×250 mL). The combined extracts were dried (Na₂SO₄), concentrated in vacuo and purified by elution from a medium pressure silica column with a blend of hexane and dichloromethane on a gradient from a 4:1 to a 1:1 ratio blend to yield the pure azide 13 (8.1 g, 79.5% yield) as a yellow oil which solidified in the freezer.

Example 29

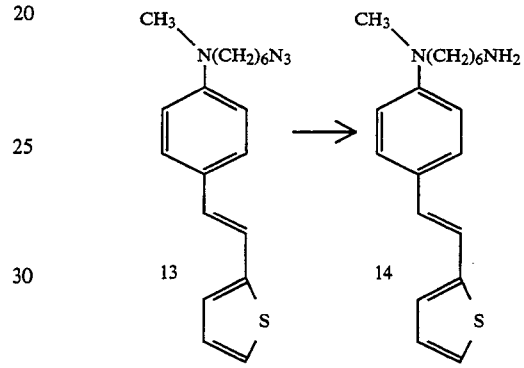

(Trans)-7-[4-(1-((6'-aminohexyl) methylamino benzene))] ethenyl thiophene 14 was synthesized by adding triphenylphosphine (1.54 g, 5.88 mmol.) to a stirred solution of azide 13 (2.0 g, 5.87 mmol.) in 30 mL of dry, freshly distilled tetrahydrofuran under argon at room temperature. The mixture was stirred for 5 hours, at which time 5 mL of water was added to hydrolyze the phosphoimine that had formed, and the resulting solution was stirred overnight. To this solution, potassium hydroxide (2 g, excess) was added and stirred for 1 hour. The mixture was concentrated in vacuo, redissolved in a blend of dichloromethane and water (25 mL each) and acidified with concentrated hydrochloric acid. The aqueous layer was extracted with dichloromethane to remove any neutrals and then basified with 50% aqueous sodium hydroxide. The basic solution was extracted with dichloromethane (2×100 mL), dried (Na₂SO₄), and concentrated to yield pure amine 14 (1.84 g, 96% yield) as a pale, yellow solid.

EXAMPLES 30-33

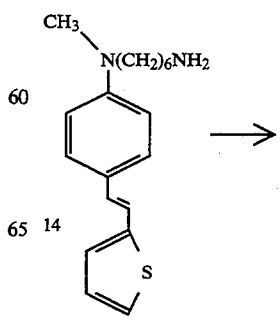

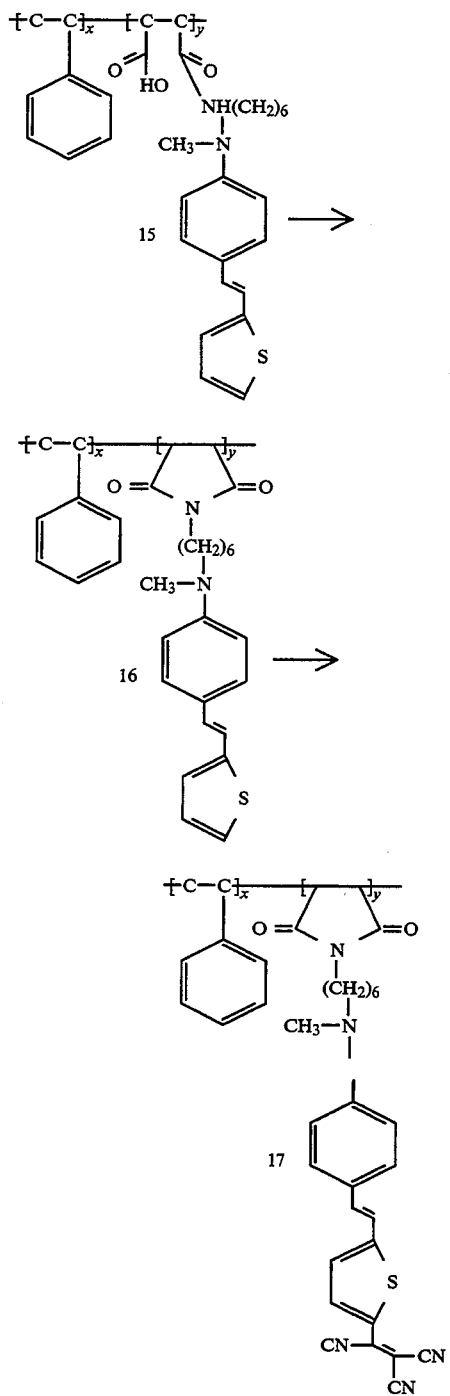

The amine 14 of Example 29 was directly attached to a polymer. As shown in Table III, poly(styrene maleic anhydride) copolymers (Arco Chemical) having molecular weights of 10,000, 50,000 and 176,000 daltons were utilized. The maleic anhydride was completely substituted, so that the degree of NLO substitution reflects the mole percent of maleic anhydride in the starting material polymer, which is depicted in Table III. In Table III, X represents the mole percentage of styrene in the starting polymer and Y represents the mole percentage of maleic anhydride in the starting polymer. The molecular weight listed is that represented by the manufacturer of the polymer. Thermal properties were determined by DSC.

TABLE III

| Example | X | Y | MW | $T_g{}^c$ | $T_g{}^d$ | $T_g{}^e$ | $T_g{}^f$ |
|---------|----|----|---------|-----|-----|-----|-----------|
| 30 | 67 | 33 | 10,000 | 111 | 132 | 126 | 147 |
| 31 | 50 | 50 | 50,000 | 160 | 136 | 165 | 115 & 150 |
| 32 | 93 | 7 | 176,000 | 109 | 113 | 103 | 116 |
| 33 | 85 | 15 | 176,000 | 114 | 122 | N/A | N/A |

$^c T_g$ of polyamic acid as determined by DSC.
$^d T_g$ of starting material as determined by DSC.
$^e T_g$ of polyimide as determined by DSC.
$^f T_g$ of tricyanovinylated polyimide as determined by DSC.

The polymers were substituted by slowly dripping a solution of the amine 14 of Example 29 in dry tetrahydrofuran into a stirred, dried tetrahydrofuran solution containing an equivalent quantity of poly(styrene maleic anhydride) copolymer. After 5 hours at room temperature, the solutions of Examples 30 and 31 were poured into vigorously stirred solutions of hexane to precipitate the polymers as white amorphous solids. The polymers were then purified by reprecipitation from dichloromethane into hexane to give the resulting product, a poly-amic acid in quantitative yield. The polymers of Examples 32 and 33 were similarly poured into methanol to precipitate the polymers as white amorphous solids that were purified by reprecipitation from dichloromethane into methanol to give the corresponding amic acid in quantitative yield.

Examples 34 and 35

The poly(styrene amic acid) copolymers of Examples 30 and 31 were converted to poly(styrene imides) by adding the polymers of Examples 30 and 31 (0.25 g) to solutions containing 3 mL of triethyl amine and 3 mL of acetic anhydride. The solutions were heated to 85°-100° C. for 12 hours and then poured into vigorously stirred solutions of methanol to precipitate the tan-colored polymers. The polymers were purified by reprecipitation from dichloromethane into methanol to quantitatively give the desired poly(styrene imides).

Examples 36 and 37

The poly(styrene amic acid) copolymers of Examples 32 and 33 were converted to poly(styrene imides) by adding dropwise to solutions of the polymers of Examples 32 and 33 (1 g) in dry tetrahydrofuran, a solution containing acetic acid (1 mL) and triethyl amine (1 mL). The mixtures were warmed to 45°-50° C. and stirred under argon overnight. The resulting solutions were cooled and slowly poured into vigorously stirred solutions of methanol to precipitate tan-colored polymers. The resulting poly(styrene imides) were purified by reprecipitation from dichloromethane into methanol to quantitatively give the desired poly(styrene imides) in quantitative yield. The properties of the polymers of Examples 34-37 are depicted in Table III.

Examples 38-41

The poly(styrene imides) of Examples 34-37 were tricyanovinylated by gradually adding (approx. 5-10 min.) quantities of tetracyanoethylene (0.64 g, excess) to stirred solutions of the poly(styrene imides) of Examples 34-37 (4.0 g) in dimethylformamide (25 mL) at room temperature under argon. The reaction mixtures were warmed to 110° C. for 6 hours. Upon cooling, the reaction mixtures were poured into 250 mL quantities of agitated water to precipitate the polymers as amorphous jade green solids. Yields were quantitative. The polymers were purified by repeated reprecipitation from dichloromethane into methanol, and then dried in vacuo (30 millitorr) at 65° C. for 48 hours. The molecular weight and thermal properties of the tricyanovinylated poly(styrene imides) are shown in Table III.

Example 42

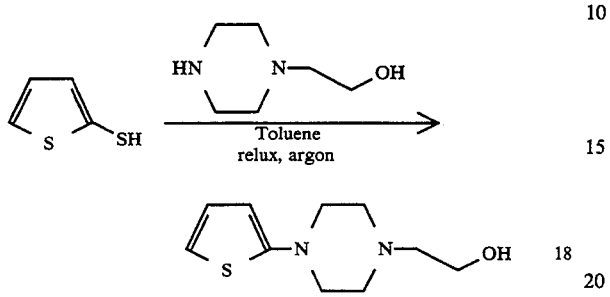

2-[1-(2'-hydroxyethyl)piperazino] thiophene 18 was prepared by warming a solution containing thiophene-2-thiol (1.16 g, 10.0 mmol.) and 1-(2-hydroxyethyl) piperazine (1.43 g, 11.0 mmol.) in toluene to reflux under an argon atmosphere for two hours. Completion of the reaction was confirmed by thin layer chromatography using a 4:1 ratio blend of hexane and ethyl acetate as the eluent. The reaction mixture was cooled to room temperature, and the solvent was removed in vacuo. The residue was then concentrated onto 5 g of silica. The silica was added to a medium pressure chromatography column packed with silica. The column was eluted with a 4:1 ratio blend of hexane and ethyl acetate to yield the pure piperazino-thiophene 18 (1.62 g, 76.4% yield) as a pale yellow solid.

Example 43

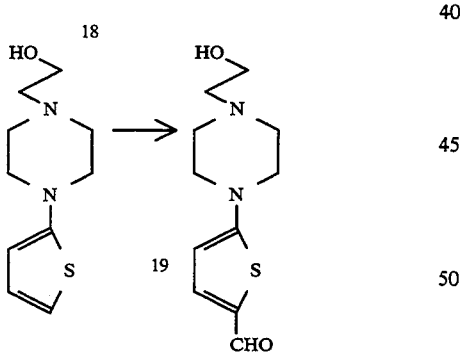

5-formyl-2[1-(2'-hydroxyethyl) piperazino] thiophene 19 was prepared by adding n-butyl lithium (8.4 mL, 21 mmol.) to a stirred solution of the piperazino-thiophene 18 of Example 42 (2.12 g, 10 mmol.) in tetrahydrofuran (50 mL) at −30° C. The reaction mixture was allowed to warm to room temperature over a 30 minute period, with stirring. The reaction mixture was stirred for another hour and then dimethylformamide (5 mL, excess) was added. After an additional hour, the reaction was quenched with water. The solution was cooled, filtered, and the solvent was removed in vacuo. The residual oil was concentrated onto 5 g of silica. The silica was added to a medium pressure chromatography column packed with silica. The column was eluted with dichloromethane to yield aldehyde 19 (2.2 g, 92% yield) as a pale yellow solid.

Example 44

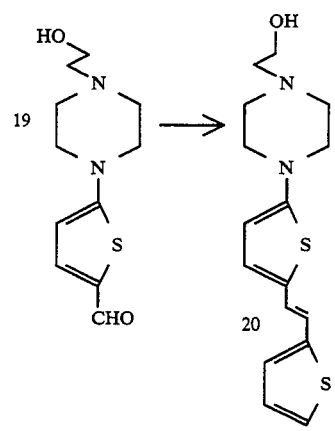

(Trans) -7-([1-(2'-hydroxyethyl)piperazino] thiophene) ethenyl thiophene 20 was prepared by adding potassium t-butoxide (0.93 g, 8.32 mmol.) to a stirred solution of the aldehyde 19 of Example 43 (2.0 g, 8.32 mmol.) and the ethyl thiophene phosphonate ester of Example 4 (1.9 g, 8.33 mmol.) in 25 mL of dry, freshly distilled tetrahydrofuran under argon at room temperature. The mixture was stirred in the absence of light for two to three hours. The mixture was then concentrated in vacuo, and the residue was dissolved in dichloromethane, washed with water (2×50 mL), dried (Na$_2$SO$_4$), and concentrated onto 5 g of silica. The silica was added to a medium pressure column packed with silica. The column was eluted with a 1:1 ratio blend of hexane and dichloromethane with a gradient to pure dichloromethane to obtain 20 (2.5 g, 94% yield) as a pale yellow solid.

Example 45

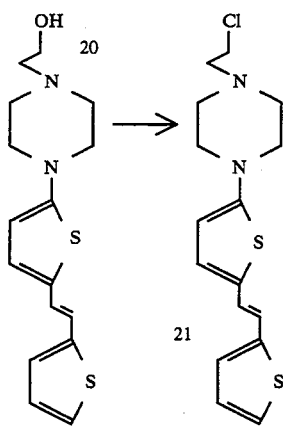

(Trans)-7-([1-(2'-chloroethyl)piperazino] thiophene)ethenyl thiophene 21 was prepared by first adding phosphorus oxychloride (1.2 g, 7.8 mmol.) dropwise at 0° C. to 3 mL of N,N'-dimethylformamide, with the resulting mixture being stirred for two hours at 0° C. To this mixture was added slowly 20 of Example 44 (2.5 g, 7.8 mmol.) in dimethylformamide (3 mL). The resulting mixture was heated to 90° C. for three hours. After cooling, the solution was poured onto 50 g of ice and the resulting material was hydrolyzed with potassium carbonate overnight. The basic mixture was extracted with dichloromethane (3×50 mL), and the organic layers were combined, dried (Na2SO4), and the solvent was removed in vacuo. The brown residue was concentrated onto 5 g of silica, which was added to a medium pressure chromatography column packed with silica. The column was eluted with a 5:1 ratio blend of hexane and dichloromethane with a gradient to a 1:1 ratio to yield 21 (2.40 g, 89% yield) as a white solid.

Example 46

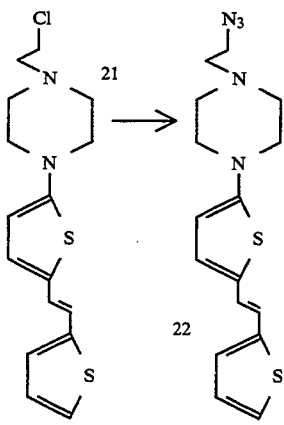

(Trans)-7-([1-(2'-azoethyl)piperazino] thiophene) ethenyl thiophene 22 was prepared by suspending sodium azide (0.66 g, 10.2 mmol.) in a solution of dimethylformamide containing the chloride 21 of Example 45 (2.4 g, 6.8 mmol.). The suspension was heated to 100° C. under argon and then water was added until everything was in solution. The reaction was maintained at 100° C. for three hours. After cooling, the solution was poured into water (100 mL) and the resulting mixture was extracted with dichloromethane (2×50 mL). The combined extracts were dried (Na2SO4), concentrated in vacuo and purified by elution from a medium pressure silica column with a blend of hexane and dichloromethane on a gradient from a 4:1 to a 1:1 ratio blend to yield the pure azide 22 (2.2 g, 87% yield) as a yellow solid.

Example 47

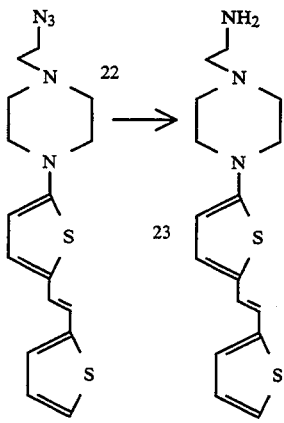

(Trans)-7-([1-(2'-aminoethyl)piperazino] thiophene)ethenyl thiophene 23 was prepared by adding triphenylphosphine (1.59 g, 6.08 mmol.) to a stirred solution of the azide 22 of Example 46 (2.2 g, 6.08 mmol.) in 30 mL of dry, freshly distilled tetrahydrofuran under argon at room temperature. The mixture was stirred for five hours, at which time 5 mL of water was added to hydrolyze the phosphoimine that had formed, and the resulting solution was stirred overnight. To this solution, potassium hydroxide (2 g, excess) was added and stirred for one hour. The mixture was concentrated in vacuo, redissolved in a mixture of dichloromethane and water (25 mL each) and acidified with concentrated hydrochloric acid. The aqueous layer was extracted with dichloromethane to remove any neutrals and then basified with 50% aqueous sodium hydroxide. The basic solution was extracted with dichloromethane (2×100 mL), dried (Na2SO4), and concentrated to yield the pure amine 23 (1.84 g, 96% yield) as a colorless solid.

Example 48

The amine 23 of Example 47 was directly attached to a poly(styrene maleic anhydride) copolymer having a molecular weight of 176,000 daltons following the procedure of Example 32 to form a poly(amic acid) 24. The poly(amic acid) 24 was then converted to a poly(styrene imide) 25 following the procedure of Example 36.

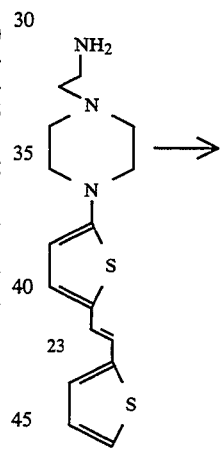

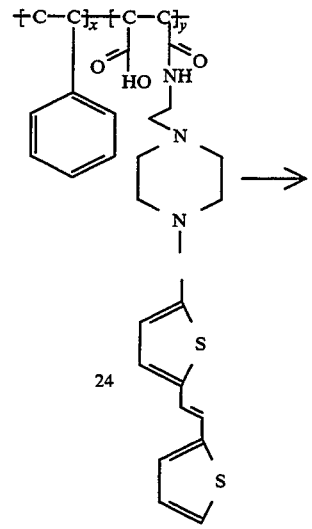

-continued

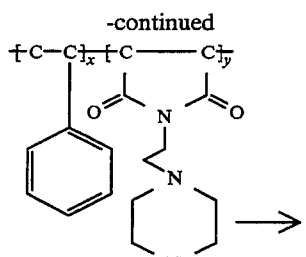

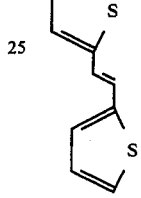

25

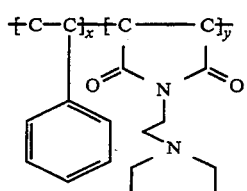

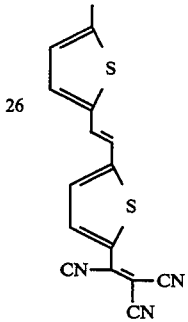

26

The poly(styrene imide) 25 was then tricyanovinylated 26 following the procedure of Example 40. The starting polymer had a styrene content of 93% and a $T_g$ of 113° C., as determined by DSC. The poly(amic acid) had a $T_g$ of 119° C., the poly(styrene imide) had a $T_g$ of 114° C., and the tricyanovinylated poly(styrene imide) had a $T_g$ of 122° C.

The foregoing examples demonstrate the versatility with which pre-NLO side chains can be attached to commercially available polymers and then tricyanovinylated to yield NLO polymers.

The foregoing description of the preferred embodiment should be taken as illustrating, rather than as limiting, the present invention as defined by the claims. Numerous variations and combinations of the features described above can be utilized without departing from the present invention.

We claim:

1. A method of preparing a polymer having second order non-linear optical properties, which method comprises the steps of:

reacting a base polymer having pendant side chains, said base polymer comprising recurring structural units represented by the formula:

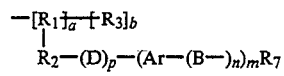

with tetracyanoethylene in a basic solvent at a temperature between about 0° C. and about 150° C., so that $R_7$ of said pendant side chains is tricyanovinylated; and recovering the resulting polymer having pendant tricyanovinylated side chains;

wherein $R_1$ and $R_3$ are monomeric subunits independently selected from the group consisting of acrylate, imide, amide, acrylamide, styrene, vinyl halide, acrylonitrile, vinyl alcohol, vinyl acetate, polyester, polyphenylene ether, polyether ketone, polyether etherketone, acid anhydride, ethylene, propylene, isobutylene, isoprene and polycarbonate monomeric subunits, wherein each $R_1$ subunit includes a functional group through which said side chains may be attached;

the ratio of a to b is between about 1:99 and about 50:50;

D comprises a first electron donating group capable of releasing electrons into said pendant side chains; p is zero or one;

$R_2$ is a straight-chained or branched alkyl, alkoxy, alkylthio or alkylamino group containing from one to ten carbon atoms attached to said monomeric subunit at said functional group, with the proviso that when p is zero, $R_2$ is attached to said functional group by an alkyl moiety and $R_2$ is an alkoxy, alkylthio or alkylamino group;

each Ar comprises an aromatic substituent independently selected from the group consisting of six-membered aromatic rings, five-membered heteroaromatic rings, fused ring systems containing at least one six-membered aromatic ring and fused ring systems containing at least one five-membered heteroaromatic ring having one heteroatom selected from the group consisting of O, N, S and Se;

$R_7$ comprises a heteroaromatic substituent selected from the group consisting of five-membered heteroaromatic rings having one heteroatom selected from the group consisting of O, N, S and Se, fused ring systems containing at least one five-membered heteroaromatic ring having one heteroatom selected from the group consisting of O, S and Se, fused ring systems containing at least one five-membered heteroaromatic ring having two to for N heteroatoms, fused ring systems containing all five-membered heteroaromatic rings having one heteroatom selected from the group consisting of O, N, S and Se, pyrimidine and purine, so that $R_7$ is tricyanovinylated at a ring position alpha to a heteroatom;

B comprises a conjugated functional group, the value of n for each B is zero, one, two or three, and m is from one to nine, inclusive; and $R_2$ or D or B are attached to a member of a heteroaromatic ring alpha to a heteroatom, and when Ar is an aromatic ring, B is attached to a member of said aromatic ring para to $R_2$ or D or another B.

2. The method of claim 1, wherein said basic solvent is selected from the group consisting of dimethylformamide (DMF), pyridine, N,N'-dimethylacetamide, N-methylpyrrolidone and tertiary amines.

3. The method of claim 1, wherein said solvent is DMF.

4. The method of claim 1, wherein the temperature of said reacting step is about 100° C.

5. The method of claim 1, wherein m of said recurring structural unit is from one to three.

6. The method of claim 1, wherein two or more heteroaromatic rings are present in said recurring structural unit, alone, or as part of a fused ring system.

7. The method of claim 6, wherein all of said rings are five-membered heteroaromatic rings, and all of said fused ring systems contain a five-membered heteroaromatic ring.

8. The method of claim 1, wherein said heteroaromatic rings of said recurring structural unit contain from two to four N-atoms.

9. The method of claim 1, wherein at least one of Ar and $R_7$ of said recurring structural unit is a fused ring system.

10. The method of claim 1, wherein B of said recurring structural unit is selected from the group consisting of —N=N—, —CH=N—, —CH=N—N=CH—, —C≡C— and (—CH=CH—)$_j$ wherein j is from one to three, inclusive.

11. The combination of claim 1, wherein $R_2$ is selected from the group consisting of (—CH$_2$—)$_x$, (—CH$_2$—R$_9$—)$_x$, (—CH$_2$—CH$_2$—R$_9$—)$_{x/2}$ and (—CH$_2$—CH$_2$—CH$_2$—R$_9$—)$_{x/3}$ wherein $R_9$ is selected from the group consisting of O, S and NH, and X is between 1 and 10, with the proviso that for (—CH$_2$—CH$_2$—R$_9$—), x is a multiple of two, and for (—CH$_2$—CH$_2$—CH$_2$—R$_9$—), x is a multiple of three.

12. The method of claim 1, wherein $R_2$ of said recurring structural unit is an alkylamino group.

13. The method of claim 1, wherein $R_2$ of said recurring structural unit contains six carbon atoms.

14. The method of claim 1, further including a second tricyanovinyl group attached to $R_7$ of said recurring structural unit.

15. The method of claim 1, wherein $R_1$ and $R_3$ are independently selected from the group consisting of acrylate, alkyl-branched acrylate, acrylamide, alkyl-branched acrylamide, styrene, alpha-alkyl styrene, vinyl acetate, polyether ketone, polyether etherketone and ethylene monomeric subunits.

16. The method of claim 15, wherein $R_1$ and $R_3$ are independently selected from the group consisting of acrylate, methacrylate, polyether ketone and polyether etherketone monomeric subunits.

17. The method of claim 1, wherein the ratio of a to b is between about 5:95 and about 40:60.

18. The method of claim 17, wherein the ratio of a to b is about 25:75.

19. The method of claim 1, wherein each Ar of said recurring structural unit is independently selected from the group consisting of pyrrole, furan, thiophene, imidazole, oxazole, thiazole, triazole, tetrazole, pyrazole, pyrimidine, purine, quinolines, carbazole, furazan, pyrazine, indole, isoindole, indazole, phenothiazine, benzotriazole, azophenanthrenes, benzene, naphthalene, anthracene and phenanthrene; and $R_7$ is selected from the group of consisting of pyrrole, furan, thiophene, imidazole, oxazole, thiazole, triazole, tetrazole, pyrazole, pyrimidine, pyrazine, purine, furazan and indazole.

20. A method of preparing a polymer having second order non-linear optical properties, which method comprises the steps of:

reacting a base polymer having pendant side chains, said base polymer comprising recurring structural units represented by the formula:

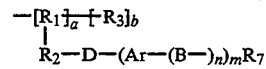

with tetracyanoethylene in a basic solvent at a temperature between about 0° C. and about 150° C., so that $R_7$ of said pendant side chains is tricyanovinylated; and recovering the resulting polymer having pendant tricyanovinylated side chains;

wherein $R_1$ and $R_3$ are monomeric subunits independently selected from the group consisting of acrylate, imide, amide, acrylamide, styrene, vinyl halide, acrylonitrile, vinyl alcohol, vinyl acetate, polyester, polyphenylene ether, polyether ketone, polyether etherketone, acid anhydride, ethylene, propylene, isobutylene, isoprene and polycarbonate monomeric subunits, wherein each $R_1$ subunit includes a functional group through which said side chains may be attached;

the ratio of a to b is between about 1:99 and about 50:50;

D comprises a first electron donating group selected from the group consisting of:

—OR$_8$, —SR$_8$, —TeR$_8$, —SeR$_8$, —CH=NR$_4$, —CH=N—NH$_2$, —CH=N—N(R$_5$R$_6$) and —CH=C[N(R$_5$R$_6$)]$_2$, wherein $R_4$ is hydrogen or an alkyl group containing up to 10 carbon atoms, $R_8$ is an alkyl groups containing up to 6 carbon atoms and $R_5$ and $R_6$ are independently selected from the group consisting of hydrogen, alkyl groups containing up to 12 carbon atoms and alkyl groups containing up to 12 carbon atoms having reactive functional groups selected from the group consisting of hydroxy, ethylene, acetylene, amine, thiol, sulfonic acid and carboxylic acid, or $R_5$ and $R_6$ together form a cyclic group containing up to 8 carbon atoms; or D comprises a first electron donating group selected from the group consisting of:

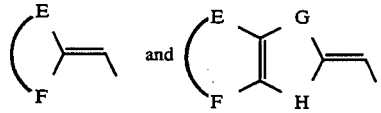

wherein E, F, G and H are members of a saturated or unsaturated five- to eight-membered ring or fused ring system which is electron donating in nature and E, F, C and H are heteroatoms independently selected from the group consisting, of O, N, S, Se and Te;

$R_2$ is a straight-chained or branched alkyl, alkoxy, alkylthio or alkylamino group containing from one to ten carbon atoms attached to said monomeric subunit at said functional group;

each Ar comprises an aromatic substituent independently selected from the group consisting of six-membered aromatic rings, five-membered heteroaromatic rings, fused ring systems containing at least one six-membered aromatic ring and fused ring systems containing at least one five-membered heteroaromatic ring, having one heteroatom selected from the group consisting of O, N, S and Se;

$R_7$ comprises a heteroaromatic substituent selected from the group consisting of five-membered heteroaromatic rings having one heteroatom selected from the group consisting of O, N, S and Se, fused ring systems containing at least one five-membered heteroaromatic ring having one heteroatom selected from the group consisting of O, S and Se, fused ring systems containing all five-membered heteroaromatic rings having one heteroatom selected from the group consisting of O, N, S and Se, fused ring systems containing at least one five-membered heteroaromatic ring having two to four N heteroatoms, pyrimidine and purine, so that $R_7$ is tricyanovinylated at a ring position alpha to a heteroatom;

B comprises a conjugated functional group, the value of n for each B is 0, 1, 2 or 3, and m is from 1 to 9, inclusive; and $R_2$ or D or B are attached to a member of a heteroaromatic ring alpha to a heteroatom, and when Ar is an aromatic ring, B is attached to a member of said aromatic ring para to $R_2$ or D or another B.

* * * * *

UNITED STATES PATENT AND TRADEMARK OFFICE
CERTIFICATE OF CORRECTION

PATENT NO. : 5,395,556
DATED : March 7, 1995
INVENTOR(S) : Drost, et al

It is certified that error appears in the above-indentified patent and that said Letters Patent is hereby corrected as shown below:

Column 1, line 37, "$P=\alpha E+\beta E^2+\gamma E^3+$" should read --$P=\alpha E+\beta E^2+\gamma E^3+\ldots$--

Column 11, lines 49-68 and Column 12, lines 14-20 and lines 37-43, Scheme 3 was separated; therefore, Scheme 3 should appear as below:.

Scheme 3

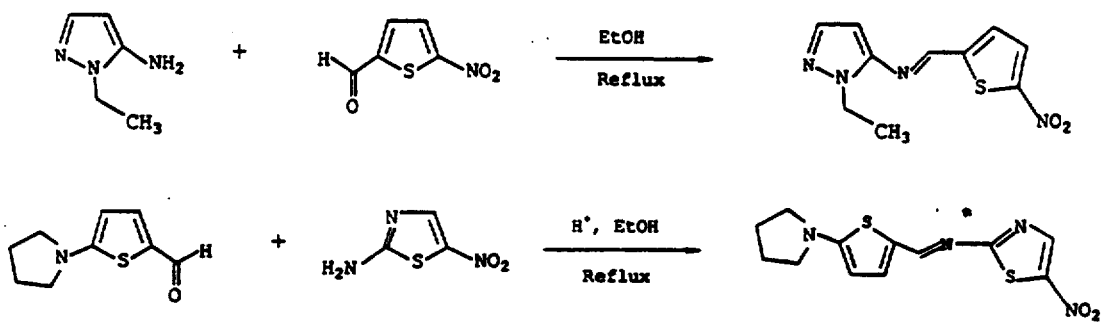

UNITED STATES PATENT AND TRADEMARK OFFICE
CERTIFICATE OF CORRECTION

PATENT NO. : 5,395,556
DATED : March 7, 1995
INVENTOR(S) : Drost, et al

It is certified that error appears in the above-indentified patent and that said Letters Patent is hereby corrected as shown below:

Column 18, line 54, "$(-CH_2)_x,$" should read --$(-CH_2-)_{x'}$--.

Column 18, line 55, "$(-CH_2-CH_2CH_2-R_9-)_{x/3},$" should read --$(-CH_2-CH_2-CH_2-R_9-)_{x/3'}$--.

Column 38, line 54, "for" should read --four--.

Column 40, line 56, "E, F, C" should read --E, F, G--.

Signed and Sealed this

Eighth Day of August, 1995

BRUCE LEHMAN

Attest:

Attesting Officer

Commissioner of Patents and Trademarks